(12) United States Patent  
Norris

(10) Patent No.: US 10,743,568 B2
(45) Date of Patent: Aug. 18, 2020

(54) DRIED FLAKES WITH ACTIVE INGREDIENTS

(71) Applicant: Flavorsense, San Rafael, CA (US)

(72) Inventor: Leslie M. Norris, San Rafael, CA (US)

(73) Assignee: Flavorsense, San Rafael, CA (US)

( * ) Notice: Subject to any disclaimer, the term of this patent is extended or adjusted under 35 U.S.C. 154(b) by 0 days.

(21) Appl. No.: 16/411,037

(22) Filed: May 13, 2019

(65) Prior Publication Data

US 2019/0261657 A1 Aug. 29, 2019

Related U.S. Application Data

(63) Continuation of application No. PCT/US2017/067135, filed on Dec. 18, 2017.
(Continued)

(51) Int. Cl.
*A23L 3/48* (2006.01)
*A23L 27/00* (2016.01)
(Continued)

(52) U.S. Cl.
CPC ............. *A23L 3/48* (2013.01); *A23F 3/14* (2013.01); *A23L 2/39* (2013.01); *A23L 2/52* (2013.01); *A23L 19/01* (2016.08); *A23L 19/18* (2016.08); *A23L 27/10* (2016.08); *A23L 27/20* (2016.08); *A23L 27/36* (2016.08); *A23L 27/60* (2016.08); *A23L 27/70* (2016.08); *A23L 29/25* (2016.08);
(Continued)

(58) Field of Classification Search
CPC ....................................................... A23L 3/48
See application file for complete search history.

(56) References Cited

U.S. PATENT DOCUMENTS

| 4,631,837 A | 12/1986 | Magoon |
| 4,861,614 A * | 8/1989 | Seaborne ............... A23L 7/139 |
| | | 426/619 |

(Continued)

FOREIGN PATENT DOCUMENTS

| EP | 1 385 595 B1 | 2/2012 | |
| JP | 2011055811 A * | 3/2011 | ............... A23L 1/30 |
| WO | WO 2010/088211 A1 | 5/2010 | |

OTHER PUBLICATIONS

Mediavilla, et al. "Essential oil of *Cannibis sativa* L. strains". Publication date 1997 from www.internationalhempassociation.org. pp. 2-4. (Year: 1997).*

(Continued)

*Primary Examiner* — Jenna A Watts
(74) *Attorney, Agent, or Firm* — Leydig, Voit & Mayer, Ltd.

(57) ABSTRACT

A process for producing a dried product, optionally in the form of a flake, the process comprising (a) combining an active ingredient with a carrier, and an optional stabilizer, to create a wet mixture, wherein the active ingredient and carrier are in a ratio of about 1:1 to about 1:250 in the wet mixture; (b) spreading the wet mixture on a belt of a thin film belt dryer with a belt temperature in the range of about 60° C.-92° C.; and (c) drying the mixture to produce a dried product with less than about 7% moisture, optionally about 2-5% moisture, and a water activity of about 0.15 and about 0.65; as well as a dried product that can be produced by the method, and related methods and compositions.

25 Claims, 15 Drawing Sheets

Related U.S. Application Data

(60) Provisional application No. 62/435,599, filed on Dec. 16, 2016.

(51) Int. Cl.

| | | |
|---|---|---|
| *A23L 27/60* | (2016.01) | |
| *A23L 33/105* | (2016.01) | |
| *A23L 19/00* | (2016.01) | |
| *A23L 27/30* | (2016.01) | |
| *A23L 29/25* | (2016.01) | |
| *A23L 2/39* | (2006.01) | |
| *A23L 2/52* | (2006.01) | |
| *A61K 31/352* | (2006.01) | |
| *A61K 36/185* | (2006.01) | |
| *A23L 27/10* | (2016.01) | |
| *A23L 19/18* | (2016.01) | |
| *A23P 10/00* | (2016.01) | |
| *A23L 27/20* | (2016.01) | |
| *A23F 3/14* | (2006.01) | |

(52) U.S. Cl.
CPC ............ *A23L 33/105* (2016.08); *A23P 10/00* (2016.08); *A61K 31/352* (2013.01); *A61K 36/185* (2013.01); *A23V 2002/00* (2013.01)

(56) References Cited

U.S. PATENT DOCUMENTS

| | | | |
|---|---|---|---|
| 5,135,122 A | 8/1992 | Gross et al. | |
| 5,338,556 A | 8/1994 | Schwab et al. | |
| 5,523,106 A | 6/1996 | Gimmler et al. | |
| 5,652,010 A | 7/1997 | Gimmler et al. | |
| 5,709,902 A | 1/1998 | Bartolomei et al. | |
| 5,802,959 A | 9/1998 | Benson et al. | |
| 6,610,335 B2* | 8/2003 | Hansa | A23L 7/101 426/93 |
| 6,627,233 B1 | 9/2003 | Wolf et al. | |
| 6,887,493 B2 | 5/2005 | Shefer et al. | |
| 2004/0022895 A1 | 2/2004 | Castro et al. | |
| 2004/0147767 A1* | 7/2004 | Whittle | B01D 11/0242 549/390 |
| 2008/0153921 A1* | 6/2008 | Petyaev | A21D 2/10 514/762 |
| 2010/0055267 A1 | 3/2010 | Popplewell et al. | |
| 2013/0337068 A1* | 12/2013 | Petyaev | A61K 9/1075 424/489 |
| 2015/0257417 A1* | 9/2015 | Woll | A23J 1/14 426/661 |

OTHER PUBLICATIONS

Chaturvedula et al. "A new diterpene glycoside from Stevia rebaudiana". Available online from Molecules, 2011, 16, 2937-2943. pp. 1-7. (Year: 2011).*

Abonyi, et al. "Quality Retention in Strawberry and Carrot Purees dried with Refractance Window System". JFS, vol. 67, Nr. 2, 2001. pp. 1051-1056. (Year: 2001).*

Jamaludin, J. et al. "Thermal studies on Arabic gum—carrageenan polysaccharides film", *Chemical Engineering Research Bulletin*, 19 pp. 80-86 (2017).

M. Rosenberg et al. "Factors Affecting Retention in Spray-Drying Microencapsulation of Volatile Materials", *J. Agric. Food Chem.*, 38, pp. 1288-1294 (1990).

Rao et al. "Formation of Flavor Oil Microemulsions, Nanoemulsions and Emulsions: Influence of Composition and Preparation Method", *J. Agric. Food Chem.*, 59, pp. 5026-5035 (2011).

Sootitantawat, A. et al. "Effect of Water Activity on the Release Characteristics and Oxidative Stability of D-Limonene Encapsulated by Spray Drying", *J. Agric. Food Chem.*, 52, pp. 1269-1276 (2004).

Baranauskiene, R. et al. "Flavor Retention of Peppermint (*Mentha piperita* L.) Essential Oil Spray-Dried in Modified Starches during Encapsulation and Storage", *J. Agric. Food Chem.*, 55, pp. 3027-3036 (2007).

Bohn, D., et al. "Development and Validation of a Dynamic Vapor Sorption-Fast Gas Chromatography-Flame Ionization Detection Method for Rapid Analysis of Volatile Release from Glassy Matrices", *J. Agric. Food Chem*, 53, pp. 3149-3155 (2005).

Chen, X. et al., "Characterization of Orange Oil Powders and Oleogels Fabricated from Emulsion Templates Stabilized Solely by a Natural Triterpene Saponin", *J. Agric. Food Chem*, 67(9), pp. 2637-2646 (2019).

Voda, A. "The impact of freeze-drying on microstructure and rehydration properties of carrot", *Food Research International*, 49, pp. 687-693 (2012).

Tang, J. et al. "Refractance Window Dehydration Technology: A Novel Contact Drying Method," *Drying Technology*, 25: pp. 37-48 (2007).

International Search Report and Written Opinion in Application No. PCT/US17/67135 dated May 11, 2018.

* cited by examiner

DRIED FLAKES WITH ACTIVE INGREDIENTS

CROSS-REFERENCE TO RELATED APPLICATIONS

This application claims priority to international (PCT) patent application no. PCT/US2017/067135 filed on Dec. 18, 2017, which claims priority to U.S. provisional patent application 62/435,599 filed on Dec. 16, 2016, the entire disclosures of which are hereby incorporated by reference.

BACKGROUND OF THE INVENTION

The encapsulation, entrapment, enrobing and drying of natural and artificial flavors, plant extracts, micronutrient as nutraceuticals, pharmaceuticals, and other active ingredients present certain challenges. Ideally, the drying is gentle so as to not volatilize, oxidize, or otherwise damage the active ingredient. Thus, freeze-drying is often used. However, freeze drying is quite expensive, non-continuous, and difficult to use industrially. On the other hand, spray drying is much more rapid, but is not as gentle. Thus, a starting material to be spray dried will often need to have 10-20% excess active ingredient to compensate for loss due to volatilization or oxidation. A further challenge is obtaining release at a desired rate of the active ingredient in an aqueous environment such as a food, or in the digestive system of an animal (e.g., a consumer of a food, supplement, or medicine that is or is produced with the dried formulation). Thus, there remains a need for improved encapsulation, entrapment, enrobing and drying of active ingredients.

BRIEF SUMMARY OF THE INVENTION

Provided herein is a process for preparing a dried composition comprising an active ingredient. According to one aspect, the process comprises combining an active ingredient with a carrier at a ratio of between 1:1 and 1:250 to create a wet mixture, spreading the wet mixture on a belt of a conductance window dryer with a belt temperature in the range of 60° C.-92° C., and drying the mixture to produce a flake with less than 7% moisture and a water activity of between 0.15 and 0.7. Also provided herein is a dried product comprising an active ingredient, a carrier and an optional stabilizer, which can be produced by the process. Related processes and compositions also are provided.

BRIEF DESCRIPTION OF THE SEVERAL VIEWS OF THE DRAWING(S)

Figure 10:
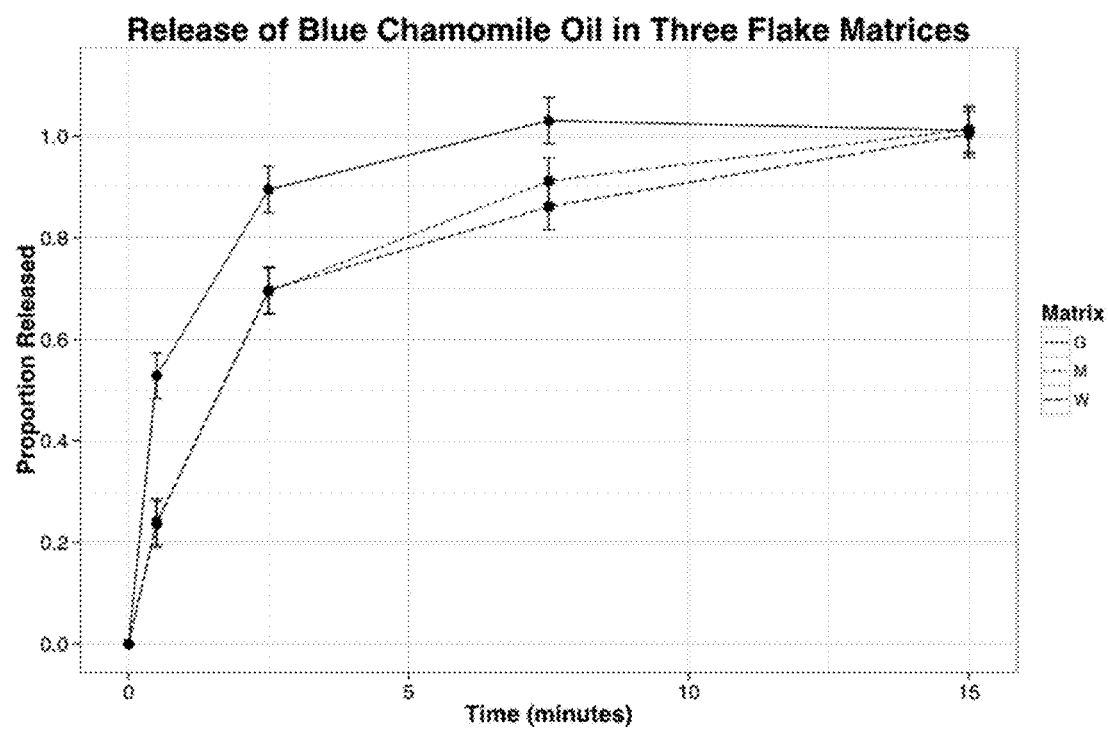

FIG. 10 shows Release of Blue Chamomile in Three Flake Matrices: G matrix is a high gum Arabic matrix, M matrix is a high maltodextrin matrix, and W matrix is a high whey protein matrix. Proportion released is the amount of blue chamomile released by the flake as predicted by the amount added to the initial emulsion. Error bars indicate 95% confidence via Tukey's Honest Significant Difference (HSD).

Figure 11:
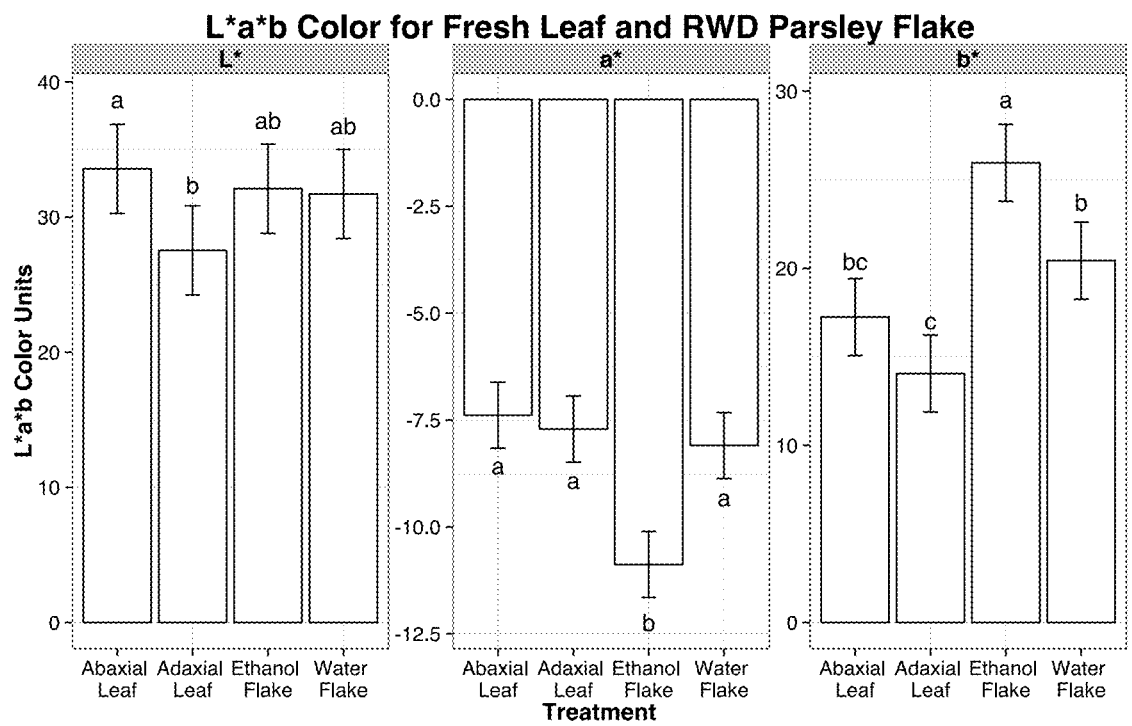

FIG. 11 shows L*a*b* Color for Fresh Leaf and RWD Parsley Flake. Adaxial and Abaxial leaf represent the two different sides of each parsley leaf. Water flake is flake with gum Arabic, parsley, and water. Ethanol flake is flake made with gum Arabic, parsley, and ethanol/water 60% (w/v). Error bars indicate 95% confidence via Tukey's Honest Significant Difference (HSD).

Figure 12:
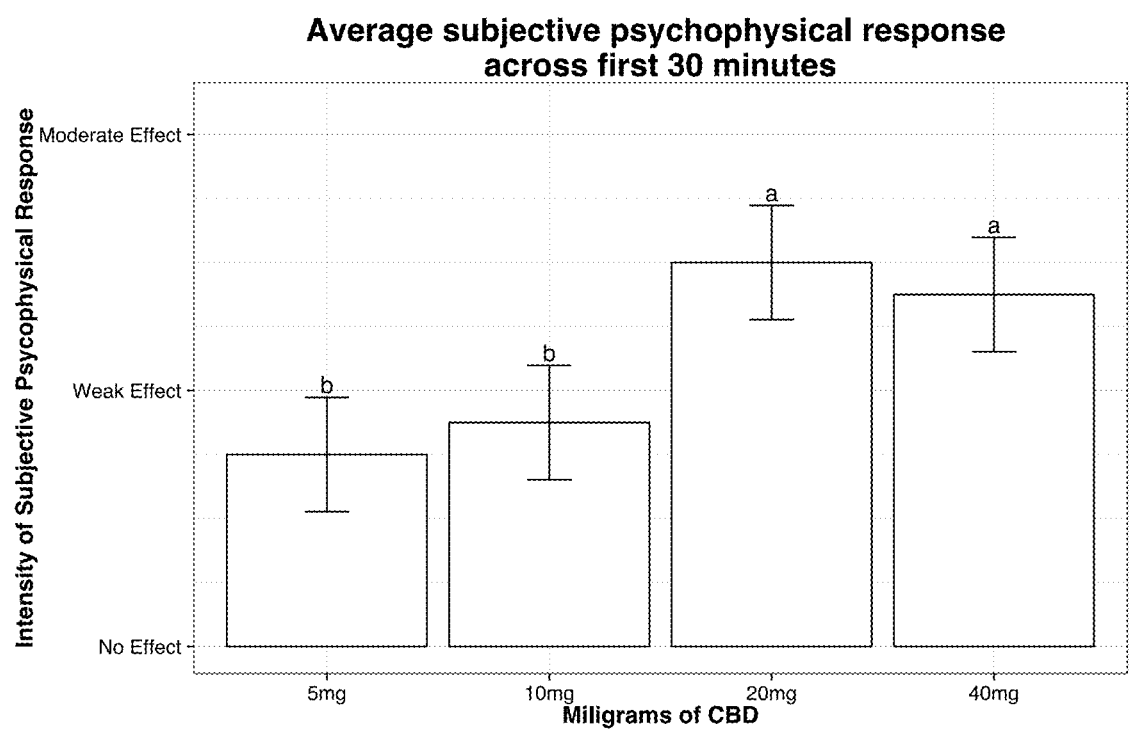

FIG. 12 shows average subjective psychophysical response across first 30 minutes. Effect strength is mean effect strength across all panelists. Error bars indicate 95% confidence via Tukey's Honest Significant Difference (HSD)

Figure 13:
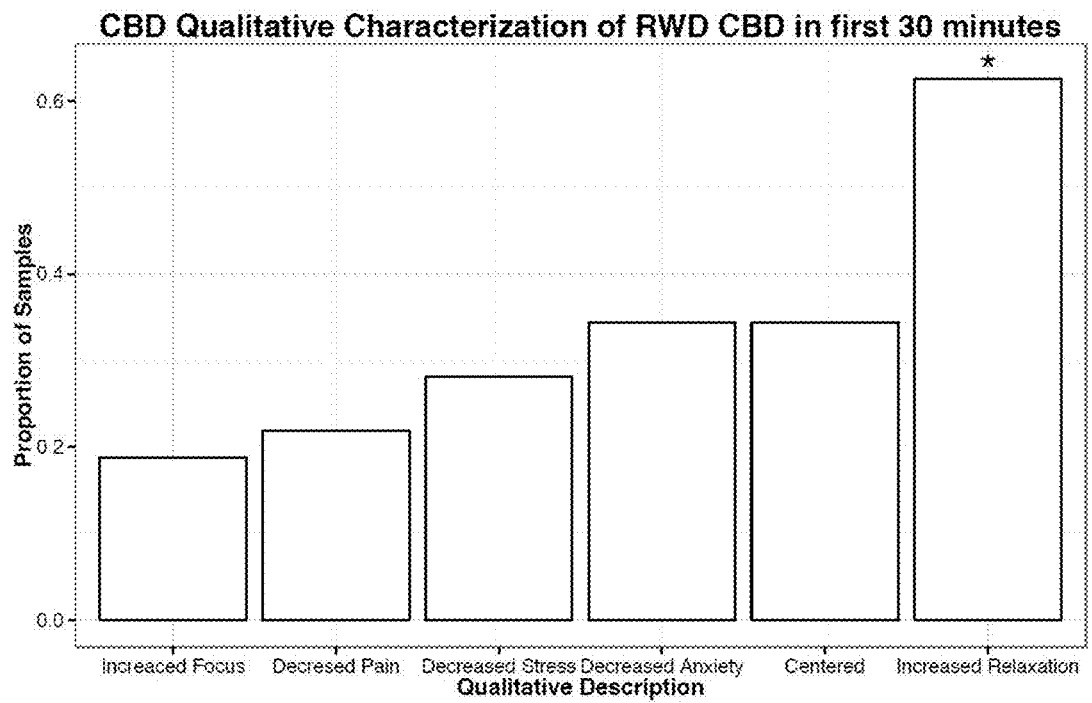

FIG. 13. shows CBD Qualitative Characterization of RWD CBD in the first 30 minutes. Proportion indicates the proportion of trials where each descriptor was deemed applicable for the qualitative feeling of CBD. Descriptors with asterisk (*) indicate that sample is significantly different from the expected usage if all descriptors were used at an equally with 95% confidence.

Figure 14:
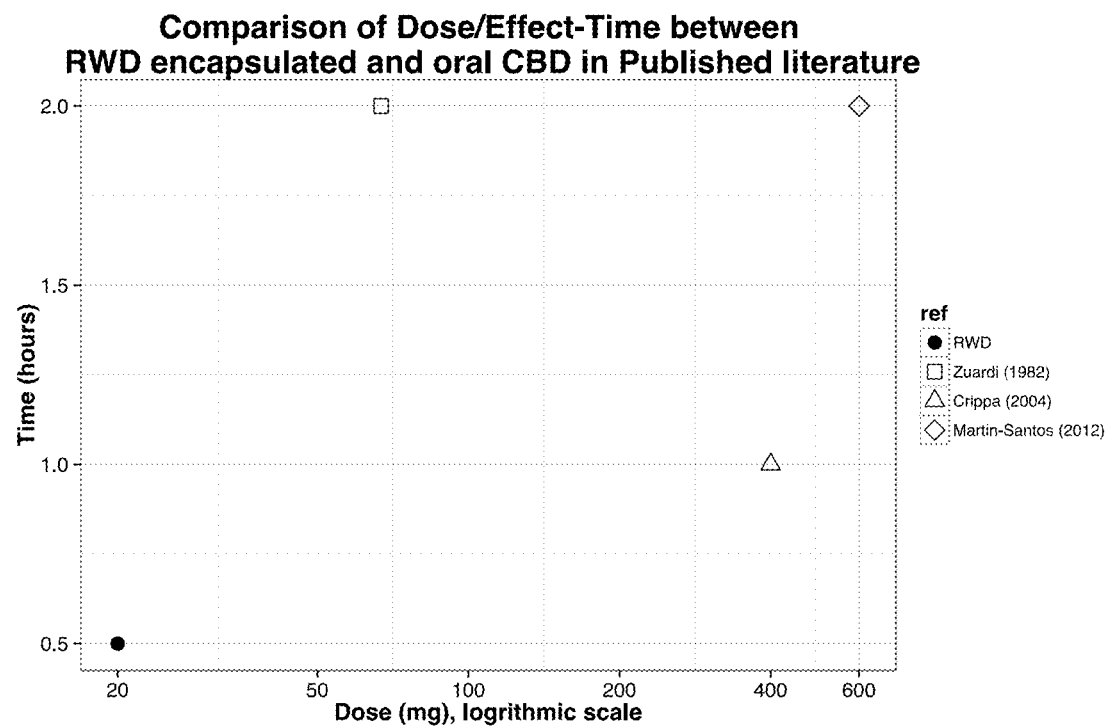

FIG. 14 shows a comparison of dose/effect-time between RWD encapsulated and oral CBD in published Literature. The filled-in symbol indicates this study, while open symbols represent orally consumed CBD in plant-based oils from literature sources.

Figure 15:
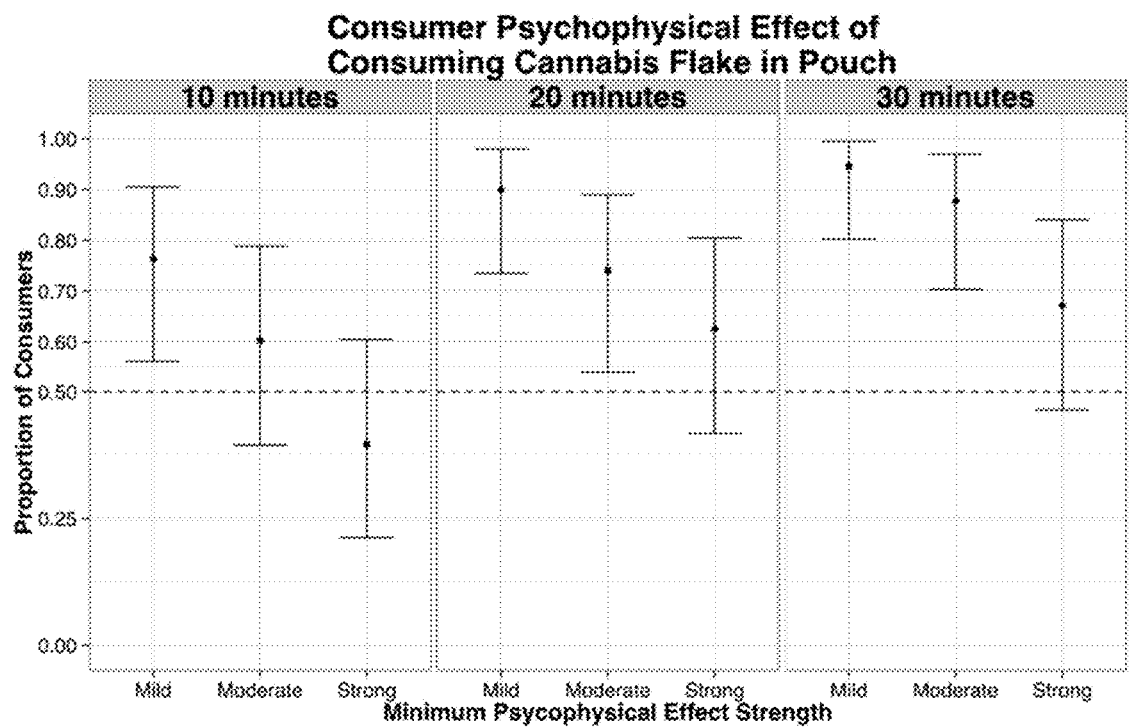

FIG. 15 shows the consumer psychophysical effect of consuming cannabis flake in a pouch. Error bars indicate 95% highest density credible interval for proportion of consumers that feel the THC product at given effect strength or stronger. Error bars above the 0.5 dashed proportion line indicate that more than half of consumers felt that effect strength or stronger at a given time-point.

DETAILED DESCRIPTION OF THE INVENTION

As used herein, "active ingredient" or "active" can be any compound or substance desired to be delivered to a subject by way of the dried product described herein. An active includes, for instance, a flavoring agent, pigment, enzyme, plant extract, plant oil, micronutrient (vitamins, carotenoids, alkaloids (such as nicotine, methylxanthines) flavonoids), nutraceuticals, cosmetic substance, or pharmaceutical substance to be dispersed and dried in a matrix. More than one active may be present, and an active may play more than one role or have more than one function in a composition. In some embodiments, the active is a biologically active compound or substance produces a physiological or psychophysical response (alteration of sensation and/or perception). Actives can be hydrophobic or hydrophilic.

In connection with a specified range, the term "between" shall be inclusive of the endpoints of the range.

A "flake" shall mean a substantially planar dried product that has a substantially planar surface and a thickness dimension (i.e. height substantially perpendicular to the plane) that is far smaller than the largest dimension of a substantially planar surface. The thickness is typically the smallest dimension of a dried product flake, and the width is the largest dimension of a substantially flat, planar side of the flake. In some embodiments, the flake has a thickness that is at least about 5 times less (e.g., at least about 10 times less, at least about 20 times less, or at least about 50 times less) than the largest dimension in the plane (width of the plane). In other words, the material has an aspect ratio (width:thickness) of at least about 5 (e.g., at least about 10, at least about 20, at least about 50, etc.). The dimensions can be determined by any technique used in the art, such as by using electronic calipers.

In connecting with a dried product, the product comprises a "glass" if it includes an amorphous material characterized by a glass transition temperature ("Tg"), e.g., as determined by differential scanning calorimetry (DSC). When the product comprises a glass, it will have a higher heat capacity above the glass transition temperature than below the glass transition temperature.

The Cannabis genus includes, Cannabis sativa, indica and ruderalis. Cannabis includes "industrial hemp" and "marijuana." A hemp or cannabis "extract" shall mean raw, purified, natural or synthetic materials commonly associated with these plants comprising cannabinoids. For example the cannabis extract can be a cannabis flower resin. Purified encompasses any degree of purification. Thus, a hemp or cannabis extract can comprise, for instance, greater than 1, 5, 10, 20, 30, 40, 50, 60, 70, 80, 95%, or even 99% cannabinoids.

The thin film belt drying can use any type of drying heat source, and typically uses conductance, convection drying, and/or infrared heat. One such method is known as "Conductance Window Drying" or "CWD," which is a process by which a wet active ingredient/carrier composition is spread on a moving belt, usually a general purpose oriented polyester (e.g. PET) belt, above a heated, temperature controlled, usually circulating, water bath (i.e., a "conductance window dryer"). Evaporated moisture over the belt is usually actively replaced with dry air. Conductance window drying is sometimes referred to as Refractance Window Drying™ (RWD) or Hydro-Dri™ (Cerule LLC). Other methods, such as Infidri™ (Powder Pure) use infrared radiation as the heating source, and still other methods use a combination thereof.

A "stabilizer" shall mean a substance that, when combined with an active ingredient and a carrier, improves the emulsion drying efficiency (e.g., how quickly a composition dries under given conditions), stabilizes the active, and/or improves the emulsion (e.g., the interaction of the active with the carrier (by decreasing stickiness, making a better dispersion, increasing emulsion stability, etc.)). In some embodiments, the stabilizer is a solvent other than water having a boiling point near the drying temperature (e.g., between 60 and 92° C., including ethanol or an ethanol/water mixture), or greater than 92° C. (e.g., various oils including stearic acid with a boiling point of 361° C.). In some embodiments the stabilizer improves the delivery of the active(s) in the final flake use.

A stable dried colloid, one type of which is an emulsion, maintains a distribution of active in the dried product over time. Thus, for instance, when a dried material (e.g., a flake) comprises a hydrophobic active dispersed in a hydrophilic material, the dispersion is "stably emulsified" the distribution of the hydrophobic active varies (e.g., due to "oiling-out") by 10% or less over a period of 6 months at 25° C. (or equivalent accelerated test). A stabile composition also is resistant to micro growth and degradation and/or loss of active. For hydrophilic actives dispersed in hydrophilic material, the resulting mixture is uniform.

A "flavoring agent" shall mean a concentrated natural or synthetic substance that imparts a flavor to a food or beverage when added.

"Carrier" shall mean an excipient that surrounds a dispersed active ingredient and carries and protects the active ingredient, and releases or otherwise delivers the active in its final use. For example, the dried active/carrier should be dispersible in a target medium (e.g., in a food, beverage aqueous or alcoholic beverage, water, or animal alimentary system). Thus carriers can be chosen based on the required properties for the intended end use of the flake. Carriers can add dispersible solids and have various film forming capacities and/or emulsifying properties in the liquid matrix. The choice of carrier will depend on the intended end-use of the product.

"Matrix" is composed of a diluent, carrier, active, and/or stabilizer, typically the entire wet mixture. The diluent can be water or combinations of alcohol and water, with alcohol not exceeding 70%, juices, desugared juice, and other liquids.

Unless otherwise specified, percent compositions described herein are based on weight (wt. %).

Provided herein is a dried product and an industrial drying process for producing the dried product from a wet mixture that includes an active ingredient, a carrier, and a stabilizer. The dried product can be used directly or further packaged, stabilized, and/or processed. Although the exemplified dried products are in the form of flakes, the dried product can also be a sheet, particle, or powder. For example, the dried product can be produced as sheets or flakes by drying and disrupted to produce particles, powders or other forms.

As discussed in the Examples below, the product of the process has surprising properties including remarkable stability in certain applications, which may be a result of a combination of the following properties of the dried product: (1) water activity, (2) glass transition temperature, (3) size of flake, (4) adsorption of water, (5) porosity of product (which is related the ability of the volatiles to escape from the product). Examples of dried products include flakes with a water-dispersible or water-soluble carrier having an encapsulated ester, terpene, cannabinoids, terpenes with cannabinoids, terpenes with esters, and terpenes with curcumin or other active ingredients. The dried products produced can be oxidation-resistant, have high active ingredient loads, have superior retention of volatiles compared to spray drying, and be less expensive to produce than comparable freeze-dried products. The dried product can be nonporous and have extremely slow fluid absorptive properties, and can have a taste, appearance or physical characteristics of the starting material. The dried product can also be substantially or completely free of any clumps or granules present in the starting material. The dried product can be stable to heat and air for years (e.g., less than 10%, 5%, or 2% loss of active ingredient per year under ambient conditions, which can be shown by extrapolation from shorter time period such as 2-week testing or by accelerated tests at higher temperatures using known relationships between temperature and stability of the active to be tested).

Figure 1:
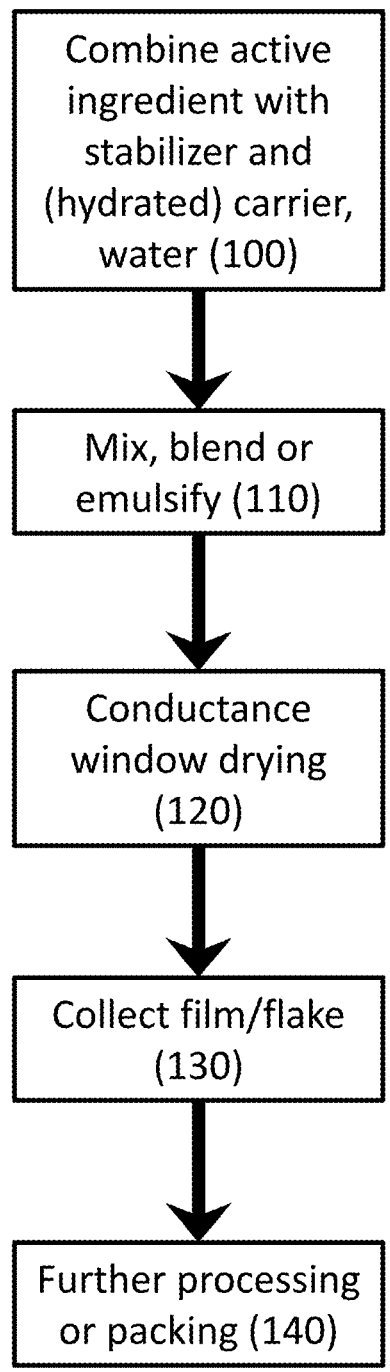
FIG. 1 is a flow chart of a process for drying an active ingredient in accordance with an embodiment.

FIG. 1 shows a flow chart of an illustrative encapsulation and drying process according to an embodiment. Active ingredient is combined with a carrier and optionally a stabilizer (step 100). For example, the active ingredient can be solubilized in the stabilizer, carrier can be added, and water can be added.

In some embodiments, the active ingredient can be a hydrophobic ingredient, the optional stabilizer can be hydrophobic, and the carrier can be hydrophilic. For example, the hydrophobic active ingredient can have a log(Kow) of greater than 0 and less than 22, more typically 0-16. The active ingredient can be also be volatile. For example, the active ingredient can have a boiling point of between 20° C. and 200° C., 75° C. and 175° C., or 100° C. and 160° C. The active ingredient can also be non-volatile. For example, the active having a melting point of between 20° C. and 200° C., 75° C. and 175° C., or 100° C. and 160° C.

The active ingredient can be a terpene or terpene glycoside. For example, the terpene can be a monoterpene such as limonene, citral, menthol, menthone, camphor, citronellol, citronellal, geraniol, gerol, alpha-pinene, beta-pinene, citral, linalool, alpha-terpineol, alpha-phllanderene, sabinene, thymol, cymene, or myrcene; a sesquiterpene such as beta-caryophylenne, alpha-humulene, or nootkatone; a diterpene such as phytol, steviol glycosides, retinol, and retinal; a triterpene such as squalene, cucurbitacin, or a mogroside glycoside; or a tetraterpene such as alpha-carotene, beta-carotene, gamma-carotene, lycopene, lutein, zeaxanthin, neoxanthin, violaxanthin, flavoxanthin, alpha-cryptoxanthin, and beta-cryptoxanthin; or any combination thereof.

In some embodiments, the active ingredient can comprise raw cannabis, an unrefined extract or refined extract of cannabis, one or more cannabinoids such as tetrahydrocannabinol (THC), cannabidiol (CBD), cannabinol (CBN), cannabigerol (CBG), tetrahydrocannabivarin (THCV), cannabidivarin (CBDV), or cannabichromene (CBC); or any combination thereof. The cannabinoid ingredient can be, optionally, a supercritical carbon dioxide, butane, hexane, water, ethanol, ethyl acetate, diethyl ether, methylene chloride, or isopropyl alcohol extract of *Cannabis*.

The active ingredient can comprise an ester; e.g., methyl esters (for example, methyl pentanoate), ethyl esters (for example, ethyl butyrate, ethyl-2-methyl butyrate, or ethyl hexanoate,), terpene esters (for example, linalyl butyrate), acetates (for example, ethyl acetate, bornyl acetate, or phenethyl acetate), etc; a well as combinations thereof.

The active ingredient can also comprise a flavoring agent, carotenoid, enzyme, alkaloid (nicotine, theobromine, theophylline, caffeine,), flavonol, phenolic compound (curcumin), botanical alcohol extract, essential oil, small-molecule pharmaceutical, nutraceuticals, vitamin, acetaldehyde, acetic acid, combinations thereof (e.g., complex flavoring), or other actives known in the art. More than one different type of active ingredient can be combined, and the active ingredient can be a combination of any of the foregoing types of actives listed, or can comprise other actives known in the art.

The carrier can comprise, for example, a gum such as gum arabic, an agar, a starch (such as maltodextrin, corn starch, potato starch, or glucomannan), inulin, a sugar (such as lactose or dextrose), oligosaccharides, a protein (such as whey or hemp protein), high protein microalgae, fermented yeast and spent grains (spent yeast from winemaking, spent grains from beer making) yeast, seed starches, whole seed and defatted seed flours, vegetable/leaf or a combination thereof (e.g., a mixture of starch and gum). The carrier can be provided in a hydrated form to create a wet mixture in the form of a solution, viscous solution, suspension or slurry. The carrier can be hydrophilic, optionally having a log (Kow) of less than 0.

Optionally, the active can be combined with a stabilizer. The stabilizer can, optionally, range in volatility, from very volatile (e.g., 77.1° C.) to nonvolatile having a high boiling point (e.g., 300° C. or greater). The stabilization may occur prior to and/or during drying such that some stabilizers (e.g., ethanol or ethyl acetate) will not be included in the final dried product in any substantial amount as the majority of the stabilizer will evaporate during the drying process. Other less volatile stabilizers will be part of the final dried product. For example, for a nonvolatile stabilizer with a boiling point of greater than 300° C. the majority of stabilizer is retained in the dried material. Still other stabilizers (e.g., some terpenes) can have an intermediate boiling point such that between 10 and 90% (e.g., 20-80, 30-70, 40-60 or about 50%) of the stabilizer remains in the dried product. In some embodiments, the stabilizer can act as a solvent for the active ingredient and/or assist in delivering the active in the flake in its final use. Examples of stabilizers include ethanol, ethyl acetate, and vegetable oil (e.g., soybean, corn oil, Canola, natural or Tailored microalgal oil (e.g. Thrive™ oil from Terravia)). Optionally, the stabilizer can be part of a more complex ingredient (e.g., vegetable oil in an oleaginous yeast or microalgae preparation).

In some embodiments, when a hydrophilic carrier such as gum arabic is used, the stabilizer can be more hydrophobic than the carrier. For example, the carrier can have a log (Kow) of less than 0 (negative number) and the stabilizer can have a log (Kow) greater than 0, and optionally between 5.1 and 16. In a specific example, the stabilizer can be a stearic acid, which is a nonvolatile stabilizer, (e.g., a majority is retained in the dried product). As discussed below, surprisingly stable formulations using active terpene with a stearic acid stabilizer have been achieved. Although stabilizers such as antioxidants can be added, these can also be omitted due to the surprising stability of the active terpene formulations made with or without the stearic acid stabilizer Any suitable ratio of carrier to active can be used. The ratio of carrier to active ingredient, or the ratio of the carrier to the active ingredient plus stabilizer ("active system"), can be in the range of about 1:1 or more, such as about 1:2 or more, or even about 1:3 or more. Generally, the ratio of carrier to active will be about 1:250 or less (e.g., about 1:100 or less; about 1:75 or less, or about 1:50 or less). In some embodiments, the ratio of carrier to active will be about 1:1 to 1:250, 1:1 to 1:20, 1:1 or 1:10, or 1:1 to 1:5. In one example of an embodiment, the wet mixture that is dried to provide a product comprises 5-50% or 5-30% (e.g., 10-50% or 10-30%) carrier (e.g., gum arabic and maltodextrin) and 0-30% (e.g., 0.1-30% or 1-30%) of a stabilizer (e.g., stearic acid), wet weight. In a specific embodiment, the wet mixture comprises 19.2% (wet weight) gum arabic and 15.3% maltodextrin as the carrier, 7.1% active, and 0.07% wet weight of stearic acid as the stabilizer. The balance can be water. In this example, the proportion by dry weight is: 35.2% gum arabic, 44.3% maltodextrin, 16.3% active 0.16% stabilizer.

An emulsifier can be included in addition to the active, carrier, and optional stabilizer. Any of a variety of emulsifiers used in food processing can be utilized in the compositions. Non-limiting examples include lecithin, polysorbates, egg yolk, and sodium stearolyl lactylate.

The active ingredient, stabilizer, and carrier are combined in any suitable manner, such as by mixing, blending or emulsifying in any order (step 110). The carrier can be premixed with water. Optionally, the active is pre-solubilized in or otherwise combined with the stabilizer. The active/stabilizer mixture can be slowly added to the wetted carrier and mixed, blended or emulsified. Optionally, additional water can be added to the active/stabilizer/carrier mixture. As a result, an oil in water emulsion with a droplet size between 0.01-20 microns in size can be formed. In an embodiment, the active ingredient can comprise 0.0001 wt. % or greater (e.g., about 1 wt. % or more, about 5 wt. % or more, about 10 wt. % or more, about 20 wt. % or more, about 30 wt. % or more) of the wet mixture.

After combining the ingredients to make the wet mixture, the mixture is spread or otherwise fed onto the belt of a thin film belt dryer/conductance window dryer (step 120). Spreading can be achieved, for example, using a spray bar or a doctor blade. Thin-film dryers are sold by, for example, G3 dryer of Modesto, Calif. and Flanders Food in Belgium. The water baths of the dryer can be set for a temperature in the range of 60° C.-92° C., 65° C.-87° C., or 70° C.-85° C. and, optionally, the dried product is cooled (e.g., to 11-21° C.).

The drying is continued until a dried product, typically in the form of a sheet or flake is produced. For example, a dried sheet (e.g., the width of the belt) can be produced on the belt, broken by the sharp edge of a knife blade and collected. In some cases, flakes will form upon drying without going through the sheet stage. The film or flake can have less than 7% moisture (e.g., 2-6%, 2-5%, or 3-5%) and a water activity of between 0.1 and 0.7, 0.1 and 0.4, or 0.15 and 0.6. Water activity can be determined, e.g., using a Novaseina R.T.D. 502 apparatus (Novaseina, Pfapfikkion, Switzerland).

The dried material can be collected from the belt (step 130) and further processed or packaged (step 140). Optionally, large pieces of the material (e.g., sheet-like pieces) are removed from the belt and broken up to form flakes or other particles of a desired size. Any size flakes or particles can be created. For some applications, the flakes or particles can be circumscribed by a circle of a diameter between 6 mm and 20 mm (e.g., 6, 7, 8, 9, 10, 11, 12, 13, 14, 15, 16, 17, 18, 19, or 20 mm). For a population of flakes or particles, the average or a majority of the flakes or particles can be can be circumscribed by a circle of a diameter between 6 mm and 20 mm (e.g., 6, 7, 8, 9, 10, 11, 12, 13, 14, 15, 16, 17, 18, 19, or 20 mm). For other applications, smaller flakes or particles might be desired (e.g., flakes or particles that can be circumscribed by a circle of a diameter of less than 6 mm, wherein the average or a majority of flakes or particles in a population have such size). Flakes can be irregular shaped and can be, for example, 1-12 mm in length, 1-6 mm width and less than 1 mm height. Optionally, the flakes can be non-porous (porosity is often correlated to volatile loss, i.e. the more porous, the more volatile loss).

As shown in the microphotographic evidence of the Examples, the flakes or particles can have globules dispersed or otherwise embedded in the carrier. The globules can comprise hydrophobic active, optionally mixed with a hydrophobic and optionally solvating stabilizer. Alternatively, the flakes can comprise hydrophobic active mixed with a hydrophilic stabilizer. The dried product produced by the process of FIG. 1 can have unique properties compared to other materials produced by thin film drying (conductance/IR), freeze drying or spray drying. In an embodiment, the dried product can have one, more than one, or all of the following properties:

(a) the dried product has a glass transition temperature between 40.5 and 80.0° C. at a water activity between 0.23 to 0.24 and optionally, a glass transition temperature between 51.7 and 68.8° C. at a water activity between 0.23 to 0.24 by differential scanning calorimetry;

(b) the dried product is a flake that appears shiny, glossy, sparkling or shimmering when compared to a comparable spray-dried composition, as determined by a human sensory panel; and an average gloss measurement of greater than 1.9 at a 60 degree angle;

(c) the active ingredient is dispersed in globules embedded in the carrier and/or remaining nonvolatile stabilizer, wherein the dried product comprises 0.1-71% optionally 1-42 wt. % or 20-40 wt. % of the active based on the weight of the dried product;

(d) the active ingredient is dispersed in globules embedded in the carrier, the globules are between 100 nm to 500 microns, predominantly less than 500, 100, 50, 20, 15 or 10 microns (e.g., 0.01-20 microns) in diameter (i.e., the majority of globules (by number) are less than 500, 100, 50, 20, 15 or 10 microns (e.g., 0.01-20 microns) in diameter as measured by electron microscopy);

(e) the dried product absorbs less than 25%, alternatively 20%, 10% water by mass when exposed to a vapor of excess magnesium chloride solution (32% relative humidity) in an air-tight container for 1 week; and less than 50%, alternatively 40%, 30% water by mass when exposed to a vapor of saturated sodium sulfate solution (81% relative humidity) in an air-tight container for 1 week;

(f) the dried product is a flake between 0.07-1000 microns thick, alternatively 10-1000 microns thick (e.g., between about 10 and 1000 microns thick); and (g) the dried product is a flake where the average flake size is 0.1-200 mm and can often be circumscribed by a circle of between about 0.6 mm and 20 mm.

In an embodiment, the dried product comprises a wet weight of 10-30% carrier (e.g., gum), and 1-20% combined active ingredient and stabilizer. In another embodiment there is a flake with a final dry weight of 1 to 46% (w/w) (e.g., 1% to 30% (w/w)) *Cannabis* extract, 54-96% (w/w) gum arabic, and 0% to 46% (w/w) (e.g., 1% to 46% (w/w)) added terpene. In a specific embodiment, the terpene is myrcene. In an embodiment, the dried product can comprise 10-30% or 20-40% cannabis oil, 50-90% (e.g., 54-80% or 56-86%) gum arabic, and/or 1 to 10 percent myrcene or other terpene. In another embodiment, the dried product can comprise 22-37% cannabis oil, 60-75% gum arabic, and/or 1 to 5 percent myrcene or other terpene. For example, the dried product can comprise 25% or 27% cannabis oil, 67% or 70% gum arabic, 3% or 4% myrcene, and 3% water.

The dried product can used directly, or as an ingredient in any type of formulation, including beverages and foodstuffs. Such formulations include, for instance, dry mixes, liquid beverages, baked goods, tablets, capsules, pouches or bags (e.g., fabric or paper pouches or bags, such as for steeping in liquid or for oral consumption, such as by retaining in the mouth and allowing the active to leach out), toothpaste, dry mixes (drink, baking, etc.), mouthwash, and/or lotions/creams, seasoning blends, hot filled sauces, tablets, capsules, or other pills, chewing gum, dressings/condiment most of which can benefit from the release properties of the flake. These properties are a result of the process of creating the flakes (matrix composition, size of flake, glass transition temperature, porosity, water activity). Slow release in a lotion allows the heat of the user's hands to solubilize the flake into the water phase of the lotion such that the flake releases the active ingredient and thus can be absorbed through the skin. For a slow-release tablet, the user's stomach acid would dissolve the tablet and the flakes within the tablet will be absorbed into via the digestive system. In addition, there is fast release of the flake in the mouth when the flakes are in a pouch designed to hold in the mouth or a tablet designed to dissolve in the mouth. The delivery of the actives are faster than expected for a lipid soluble active as measured using the consumer psychophysical response test. The flakes can also be packaged for use in dry mix beverages, including in tea bags (i.e., encased in a submersible filter material). Optionally, the flake in the tea bag dissolved in water (hot, warm, or cold) but the active ingredient when put into the application remains dispersed, and does not oil-out because it is a stable colloidal dispersion (one type of which is an emulsion) upon rehydration The dried product produced by the process of FIG. 1 can have unique properties compared to other materials produced by thin film drying (conductance/IR), freeze drying or spray drying. The dried product can have one, more than one, or all of the following properties:

(a) the dried product has a glass transition temperature between 40.5 and 80.0° C. at a water activity between 0.23 to 0.24 and optionally, a glass transition temperature between 51.7 and 68.8° C. at a water activity between 0.23 to 0.24 by differential scanning calorimetry;

(b) the dried product is a flake that appears shiny, glossy, sparkling or shimmering when compared to a comparable spray-dried composition, as determined by a human sensory panel; and an average gloss measurement of greater than 1.9 at a 60 degree angle;

(c) the active ingredient is dispersed in globules embedded in the carrier and/or remaining nonvolatile stabilizer, wherein the dried product and comprises 0.1-71 wt. %, 1-50 wt. %, 1-42 wt. %, or 20-40 wt. % of the active based on the weight of the dried product;

(d) the active ingredient is dispersed in globules embedded in the carrier, the globules 100 nm-500 um, predominantly less than about 500, 100, 50, 20, 15 or 10 microns (e.g., 0.01-20 microns) in diameter (i.e., the majority of globules (by number) are less than 500, 100, 50, 20, 15 or 10 microns (e.g., 0.01-20 microns) less than a than microns size in diameter as measured by electron microscopy);

(e) the dried product absorbs less than 25%, alternatively 20%, 10% water by mass when exposed to a vapor of excess magnesium chloride solution (32% relative humidity) in an air-tight container for 1 week; and less than 50%, alternatively 40%, 30% water by mass when exposed to a vapor of saturated sodium sulfate solution (81% relative humidity) in an air-tight container for 1 week;

(f) the dried product is a flake between 0.07-1000 microns thick about 1 and 2500 microns thick (e.g., between about 10 and 1000 microns thick); and (g) the dried product is a flake with average size of 0.1-200 mm, sometimes circumscribed by a circle of between about 0.6 mm and 20 mm (e.g., between about 6 mm and 20 mm).

In an embodiment, the dried product is produced that comprises a wet weight of 10-30% carrier (e.g., gum), and 1-20% combined active ingredient and stabilizer. In another embodiment there is a flake with a final dry weight of 1 to 46% (w/w) (e.g., 1% to 30% (w/w)) *Cannabis* extract, 54-96% (w/w) gum arabic, and 0% to 46% (w/w) (e.g., 1% to 46% (w/w)) added terpene. In a specific embodiment, the terpene is myrcene. In an embodiment, the dried product can be comprise 10-30% or 20-40% cannabis oil, 50-90% (e.g., 54-80% or 56-86%) gum arabic, and/or 1 to 10 percent myrcene or other terpene. In another embodiment, the flake dried product can comprise 22-37% cannabis oil, 60-75% gum arabic, and/or 1 to 5 percent myrcene or other terpene. For example, the dry product (e.g., dried flake) can comprise 25% or 27% cannabis oil, 67% or 70% gum arabic, 3% or 4% myrcene, and 3% water.

The dried product can be formulated into a tablet, capsule, pouch, mouthwash, toothpaste, foods/beverages (baked good, drinks, etc.) and/or lotion using known techniques and optional excipients. The tablet, capsule, or lotion can be administered to a subject. In the case of medical use, the subject can be one in need of the active ingredient. The dried product can include cannabinoid, carrier and stabilizer as described above. When formulated into a topical composition such as a crème or lotion, the composition can be applied to the skin. In some cases, including the use of cannabinoid and terpene, the active ingredient can be adsorbed in the mouth through a flake containing pouch or a dry mix drink The active is absorbed and the psychophysical response to the active is felt by the consumer in 15-30 minutes, shorter than the typical 1.5-2 hrs for the active in a non-flake form.

The following examples further illustrate the invention but, of course, should not be construed as in any way limiting its scope.

In accordance with another embodiment of the present invention, a pureed food, plant starting material, or other material to be dried is combined with a carrier, and/or a volatile/hydrophilic stabilizer such as ethanol or ethyl acetate and subjected to the thin film belt drying process. The starting material can have an enzyme that causes color change (e.g., browning), oxidation, or flavor degradation in the staring material that occurs before or during drying. Optionally a puree is combined with a flavoring before drying. The volatile/hydrophilic stabilizer can be an ethanol-water mixture (e.g., about 6-95%, about 6-35%, about 10-45%, about 15-40%, or about 20-40% ethanol), or can be created via fermentation of the starting material. Optionally, the starting material is a colored plant material. Optionally, the starting material has less than 3% ethanol prior to adding ethanol as a volatile/hydrophilic stabilizer. The starting material can be, for instance, macerated in an ethanol-water mixture. The macerated material is then dried using a thin film belt dryer to produce a dried product (e.g. flakes). Surprisingly, a more natural color (e.g., green vegetable/chlorophyll color) can be obtained relative to subjecting the starting material to spray drying, freeze-drying, or CDW drying without the volatile/hydrophyllic stabilizer.

In producing such a composition, the water baths of the conductance window dryer can be set for a temperature in the range of about 60° C.-92° C., about 65° C.-87° C., or about 70° C.-85° C. and cooled prior to removal of the dried product to about 15-21° C. The range of ethanol can be from about 1-50% or from about 3-35%. In accordance with an embodiment, a fresh green plant starting material (e.g., food "vegetable" leaf/stem) is pureed in about 6-50%, about 6-35%, about 10-45%, about 15-40%, or about 20-40% ethanol and dried by CDW drying. In some embodiments, the resulting dried material has an L*a*b* color for which the l, a, and b parameters each vary by less than or equal to 10, 8, 7, 6, 5, 4, 3, 2, or 1 from that of the starting material.

Without wanting to be bound by any particular theory or mechanism of action, it is believed the addition of a volatile/hydrophyllic stabilizer such as ethanol can inhibit the activity of enzymes in the starting material, thereby preserving the color or flavor of a starting material before and during thin film drying. While ethanol has been associated with volatilization of flavors during spray drying, surprisingly, flavor and color are not significantly lost when the starting material is combined with ethanol prior to thin film drying (e.g., less than 10, 9, 8, 7, 6, 5, 4, 3, 2, or 1% loss of a desired flavor compound as determined by GC-MS and organoleptic measurements).

Example 1: Retention of a Volatile Active in a Flake

Since the carrier and active are heated at temperatures lower than used for spray drying, more of the heat sensitive actives such as citral can be retained in a flake produced by the process of FIG. 1. In a comparison to a lemon flavor encapsulation (containing lemon oil), using the same matrix, the thin film drying was able to retain 158 ppm of citral whereas spray drying the same flavor (and same matrix) retained 111 ppm. Similarly, menthol and a compounded peppermint flavor were retained at a higher rate. Typically menthol in a spray dried flavor is retained at 20%, and the thin film dryer was able to retain 26-28% menthol.

Example 2: Retention of Botanical Essential Oil Containing Oil Soluble Actives at High Loads Using the process of FIG. 1, higher than expected concentration of actives of essential oils, typically 1%-25% but as high as 42% were obtained in the final dry flake without degradation or loss of flavor One fold lemon oil, full of unstable terpenes, can be dried and stabilized. (typically the industry removes terpenes from oils to prevent off-note formation) Thus, depending on the matrix, active loads of 3.3 to 42% have been achieved, thus decreasing the usage level needed to impart the flavor/active in a finished food/nutraceutical application. Typical usage levels of spray dried flavors are 0.2-1.0% and typical usage levels of thin film dried flavors can be 0.05-0.5% due to their high concentration. The use of the process of FIG. 1 results in a similar cost in use to spray dried flavors and or vacuum freeze dried flavors.

Example 3: Retention of Botanical Extracts (e.g. Hexane, CO2, Butane, Water Extraction Methods Containing Oil and/or Water Soluble Compounds Forming a Dried Stable Colloid e in Flake Form Using the process of FIG. 1, high loads of extract were obtained without degradation of terpenes or actives. Typically 0.001-25%, but as high as 30% in some cases, were obtained in the final dry flake without degradation of terpenes, flavor or active loss. Thus depending on the matrix, active loads of 0.001-30% have been achieved with and without the use of a stabilizer, thus creating a cost effective delivery system for actives in a dry stable form.

Example 4: Formation of an Emulsion after Rehydration in Water

A mixture of non-volatile diterpenes were encapsulated using the process detailed in FIG. 1. Two protocols were used to analyze this flake, the first directly rehydrated the flake in a methanol solvent, the second rehydrated the flake than broke the emulsion with methanol prior to analyzing. The details for this experiment are detailed in the table below.

| Diterpene | Direct Analysis Concentration (mg/g) | Emulsified Analysis Concentration (mg/g) |
|---|---|---|
| #1 | 95.0 | 208.6 |
| #2 | 4.3 | 9.6 |
| #3 | 0.9 | 1.3 |
| #4 | 2.9 | 6.7 |
| #5 | 1.3 | 2.4 |

The lower observed concentration associated with direct analysis of flake is evidence that the material is encapsulated. The higher observed concentration seen post-hydration and breaking of apparent emulsification indicate that the emulsion re-formed when the flake was rehydrated.

Example 5: Characterization of the Flake vs. Freeze Drying and Spray Drying

Figure 2A:
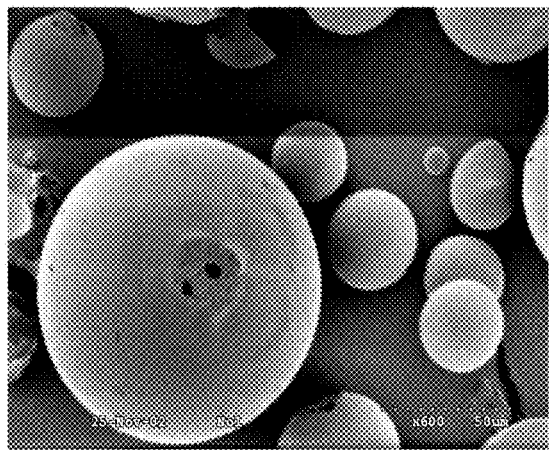
FIG. 2A is an electron micrographs illustrating the spray dried partial encapsulation of the oil droplets at 600× magnification.
Figure 2B:
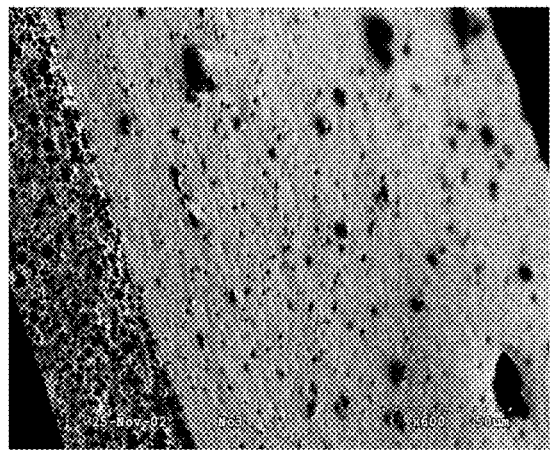
FIG. 2B is an electron micrograph at 600× magnification illustrating encapsulation of small oil droplets in a matrix of a flake produce by the process of FIG. 1.
Figure 2C:
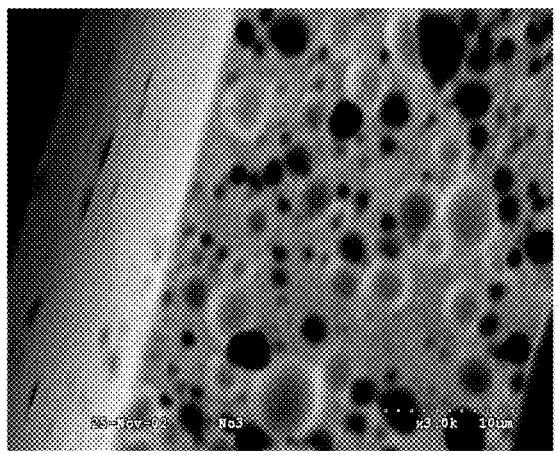
FIG. 2C is an electron micrograph at 3000× magnification of a conductance window dried lemon flavoring flake.
Figure 2D:
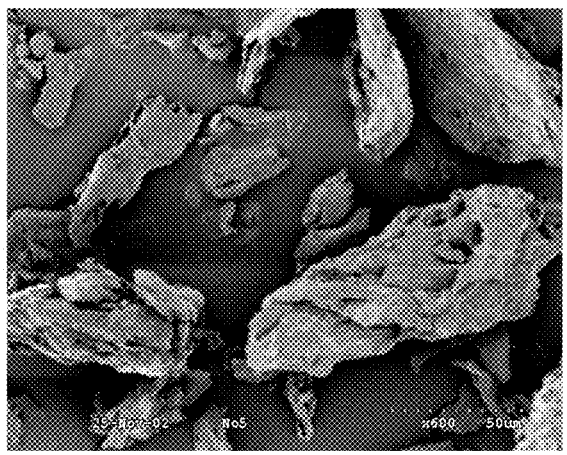
FIG. 2D is an electron micrograph at 600× magnification shows a freeze dried sample.

FIGS. 2A-2D are electron micrographs illustrating the differences between spray dried, conductance window dried and freeze dried flavors. Spray dried partial encapsulation of the oil droplets surrounded by carrier creating large spheres are shown in FIG. 2A at 600× magnification. Conductance window dried encapsulation of very small oil droplets entrapped in a matrix is shown in FIG. 2B. (600×) and FIG. 2C (3000×). The latter figure shows a conductance window dried lemon at 3000× magnification. The small (less than 10 um) oil droplets are embedded in the gum arabic matrix yielding a well encapsulated flavor. By way of comparison, as shown in FIG. 2D, a freeze dried sample shows large chunks composed of many layers (Freeze drying takes 22-48 hours typically and results in a porous, hygroscopic dried chunk.

Example 6: Iridescent/Shiny Nature of the Flake as Measured by Sensory Panelists Twelve experienced sensory panelists used a check all that apply sensory methodology for visually testing two conductance window dried samples one pink (strawberry flavored), one white in color (made by the process of FIG. 1), one spray dried sample, and three different texture powdered crystalline substances (Kosher salt, sparkle sugar and Maldon sea salt). The strawberry conductance window dried sample was made using strawberry puree (67% wet weight), gum arabic (5.6% wet weight), flavor (5% wet weight) and the remainder water. On a dry weight basis, this equates to 26% gum arabic, 46.7% strawberry, 23.25% flavor and 4% water. The finished flake was a very pleasing pink/red color. The white colored flake was vegetable oil and gum arabic at a ratio of 10% oil, 40% gum arabic with the remainder as water (wet weight) and as a dry flake correlates to 19.6% (w/w) oil, 76.4% (w/w) gum arabic, 4% water (w/w); the flakes were made according to the process of FIG. 1.

Figure 3:
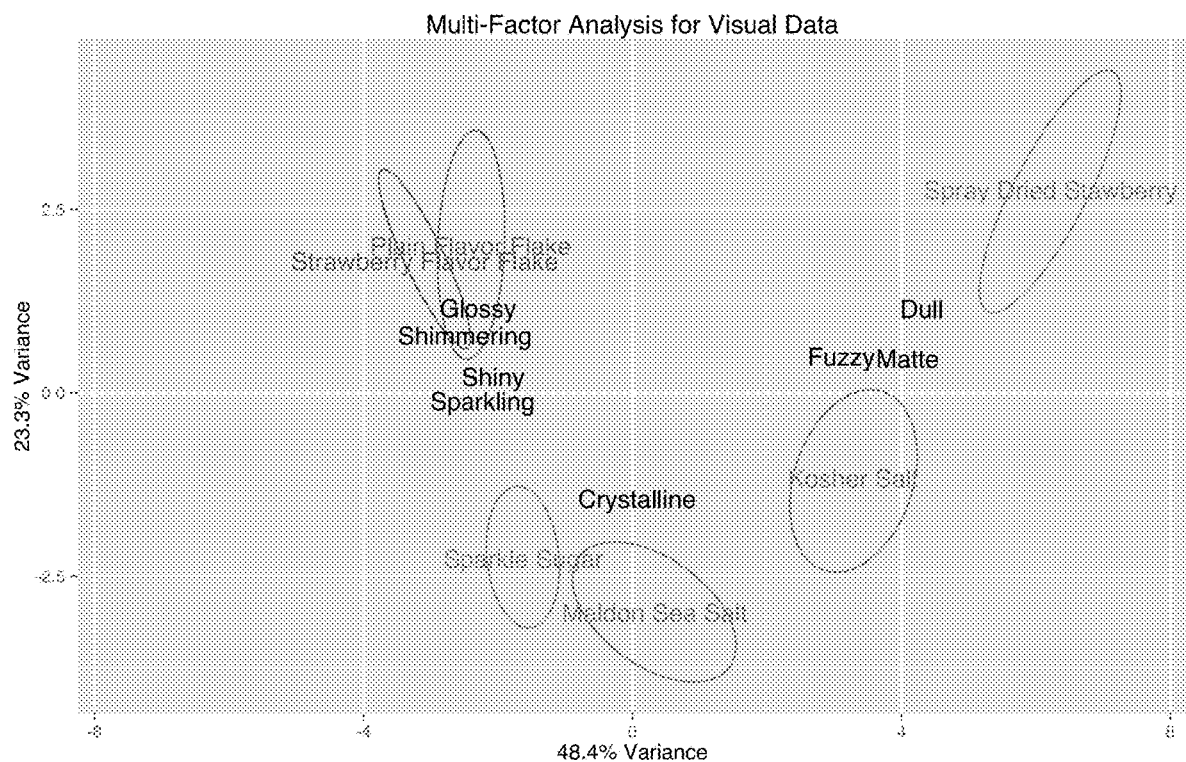
FIG. 3 shows a multi-factor analysis of visual data based on a sensory panel evaluation of a flake produced by the process of FIG. 1 compare to various dried flavors and food ingredients.

A Multi-factor analysis (MFA) biplot of visual panel data is presented in FIG. 3. Using this sensory methodology, the panelists identified that the sample ("Flavor-flake" in FIG. 3) dried according to the process of FIG. 1 was visually described as shiny, glossy, sparkling, and shimmering while the spray dried sample was described as dull.

Example 7: Instrumental Measure of Shimmer/Gloss

CWD Strawberry Flakes and Commercially Obtained Strawberry Spray Dried Powder (Blue Pacific Flavors) were compared using an ETB-0833 gloss meter at a 60 degree angle. Both encapsulated flavors were spread out on smooth piece of corrugated cardboard in order to fully cover the measurement area. Ten measurements across the surface of each flavor were taken and are reported in Table 1 along with their 95% confidence intervals. These two products have significantly different gloss at $p<0.0001$.

TABLE 1

|  | Average Gloss (GU) |
| --- | --- |
| CWD Flake | 4.5 ± 1.0 |
| Spray Dried Powder | 1.5 ± 0.4 |

Example 8: Glass Transition Temperature (Tg) of Flakes

The glass transition temperature (Tg) can be defined as the temperature at which an amorphous system changes from a glassy to a rubbery state and constitutes a reference temperature that relates physical properties to water content and temperature. Loss of aroma strength due to volatile release may occur when an encapsulated flavor transforms from the glassy state into the rubbery state. This state change can be caused by either an increase in moisture content or temperature. Typically, the Tg peak on the first heating is not read, and the second Tg reading is used (this eliminates the relaxation enthalpy that can interfere with determining Tg). An unusually small Tg peak was observed for the first heating for the CWD flake. Table 2, below, contains Tg and water activity values for three CWD flakes and typical values for spray dried flavors. The conductance window dried flavors utilized in this test were prepared as presented in below in Example 6. The spray dried values were summarized from the literature.

TABLE 2

|  | Tg | Aw |
| --- | --- | --- |
| Gum Arabic | 58.9 | 0.23 |
| Gum Arabic + Vegetable Starch | 62.2 | 0.24 |
| Gum Arabic with no stabilizer | 59.7 | 0.24 |
| Typical Spray Dried #1 | 30.7 | 0.52 |
| Typical Spray Dried #2 | 20.4 | 0.63 |

The water activity of the dried flake is substantially lower than the typical spray dried flavor as well as the glass transition temperature being substantially higher. This indicates that the thin film dried flake is more stable.

Example 9: Using Flake Technology to Deliver Fresh Flavor in a Food ApplicationSensory Analysis of cilantro Flavor Flakes in Ranch Salad Dressing Flavor actives were combined in such a manner as to create an oil-soluble fresh cilantro flavor. The flavor actives were solubilized in vegetable oil and then mixed with prehydrated gum arabic/maltodextrin at 3.5, 21.5, and 1.5% respectively. The mixture was shear-mixed using a Silverson Shear Mixer at speed 6-7. The resulting emulsion was dried on a thin film belt dryer at 180-185° F. at a belt speed of 30 percent (approximately 4.1 meters/min). For this and other Examples herein 100 pct belt speed is about 13.7 meters/min. The resulting dried flake contained 10.6% flavor, 2.2% stabilizer, 83.6% carrier and 3.6% moisture.

Twelve food scientists evaluated four methods of cilantro processing in ranch dressing. The four processed methods were flavor flakes (0.075%), air dried cilantro (0.25%), freeze dried cilantro (0.25%) and freshly chopped cilantro (2.0%). All dressings were aged 48 hours after the addition of the cilantro prior to testing. The food scientists tasted all ranch dressing using unsalted kettle potato chips and ranked them in fresh cilantro flavor. The fresher the cilantro flavor, the lower the rank. Data were analyzed using Friedman's test with least significant difference testing to determine differences. Results are presented in Tables 3. Products that share the same letter are not significantly different.

TABLE 3

| Processing Method | Average Rank | LSD separation ($\alpha = 0.05$) |
| --- | --- | --- |
| Flavor Flake (CWD) | 1.50 | A |
| Fresh Cilantro | 2.33 | Ab |
| Air Dried Cilantro | 2.67 | Bc |
| Freeze Dried Cilantro | 3.50 | C |

A comparison of cost effective usage of flavor flakes to deliver fresh flavor is presented in Table 4.

TABLE 4

| Ingredient | Cost ($) | Mass (g) | $ per g | Usage | Cost per gram dressing | Cost ($) per 500 grams dressing |
| --- | --- | --- | --- | --- | --- | --- |
| Freeze Dried | 5 | 10 | 0.50 | 0.00250 | 0.00125 | 0.63 |
| Air Dried | 7 | 15 | 0.47 | 0.00250 | 0.00117 | 0.59 |
| Flavor Flake (CWD) | 960 | 1000 | 0.96 | 0.00075 | 0.00072 | 0.36 |

Therefore, the thin film drying process produces a superior product in terms of perceived freshness, at lower cost.

Example 10: Model Flavor Flakes

A model flavor was created to investigate the properties of various matrix materials on the retention of active (flavor) compounds. In particular, the impact of whole food (microalgae or yeast) ingredients on encapsulation of volatiles in the flavor-flake was investigated. The model flavor contained the following:

| Chemical Compound | Concentration added |
| --- | --- |
| Ethyl Butyrate | 5 mg/L |
| Cis-3-hexenol | 10 mg/L |
| Limonene | 2 mg/L |
| 2-isobutyl thiazole | 1 mg/L |
| Linalool | 20 mg/L |

This model mixture was encapsulated at 11% wet weight in five different encapsulation matrices, which are as follows:

Control Matrix

| Ingredient | Wet Weight (%) | Dry Weight (%) |
|---|---|---|
| Gum Arabic | 2 | 7.1 |
| Maltodextrin | 15 | 53.6 |
| Flavor | 11 | 39.3 |
| Matrix Control | | |
| Control + microalgae at 0.5% (wet) | | |
| Control + microalgae at 4.0% (wet) | | |
| Control + Yeast at 0.5% (wet) | | |
| Control + Yeast at 4.0% (wet) | | |

Sample Matrix

Matrix components were mixed with shear with water, and model flavor slowly added while shear mixing (Silverson mixer setting 6-7). The resulting emulsion was dried at 180-185° F. at a belt speed of 22%. For this and other Examples herein 100% belt speed is about 13.7 meters/min. A 500 mg portion of flake was reconstituted in 5 mL of water and the relative concentration of each compound was measured using HS-SPME-GC-MS in triplicate. An analysis of variance was conducted on the relative measurement of each compound. Orthogonal contrasts were created to ascertain the effect of adding a whole ingredient the difference between algae and wine lees, and the effect of increasing the concentration of each whole food ingredient. The following table summarizes the results:

TABLE 3

| Matrix Comparison | 2-IB-Thiazole | cis-3-hexanol | Ethyl Butyrate | Limonene | Linalool |
|---|---|---|---|---|---|
| All treatments vs. Control | 14.72*** | 2.03** | Inf†*** | 0.52 | 3.08** |
| Microalgae (trt #1 & trt 2) vs. Yeast (trt #3 & trt #4) | 1.32* | 0.76 | 1.67*** | 0.79 | 1.33 |
| 4% (trt #2) vs. 0.5% (trt #1) in Microalgae | 1.67** | 2.38** | 1.78*** | 0.80 | 1.72* |
| 4% (trt #4) vs. 0.5% (trt #3) in Yeast | 0.91 | 0.75 | 1.96*** | 0.51 | 0.72 |

†indicates that this compound was not present in the control
*indicates significance at p < 0.05, at p < 0.01, and *at p < 0.001. Numerical values indicate proportion increase in compound concentrations between treatments.

Results indicate that the retention, as measured by higher concentration, of 4 of the 5 monitored compounds were affected by the matrix composition. In all cases where there was a significant effect the whole food (microalgae and yeast) increased encapsulation. In all cases where there was a significant effect the use of microalgae in the matrix resulted in higher retention as compared to the yeast.

Example 11: Stabilization of Active as Measured via Water Absorption

A typical industrial method of measuring the stability of a dried particle/flake is to measure the amount of water absorbed by particle/flake over time.at three different relative humidites. This gives a measure of how physically stable the dried particle/are in the presence of a given high relative humidity.

Beta carotene (active) was dissolved in a vegetable oil stabilizer 0.05 into 9.95 w/w. The active mixture was mixed with a prehydrated mixture of water and gum arabic (80/20 w/w). The resulting mixture was shear mixed using a Silverson shear mixer speed setting 6-7, and dried in a conductance window dryer. The temperature was 175° F. and belt speed was 25%. Initially the moisture content of the flavor flake was measured in triplicate using a water balance. 2.0 grams of flavor flakes were placed in each of three plastic Petri dishes inside a sealed container with a medium to control the relative humidity. The three media are as follows: silica gel (0% relative humidity), saturated magnesium chloride solution (32% relative humidity), saturated sodium sulfate solution (81% relative humidity). The flakes were allowed to equilibrate in the sealed containers for 1 week. To measure water absorption the water concentration from a sample in each Petri dish was measured using a water balance. The difference between the initial measure of water content and the water content at the end of the storage determines how much water was absorbed.

Figure 4:
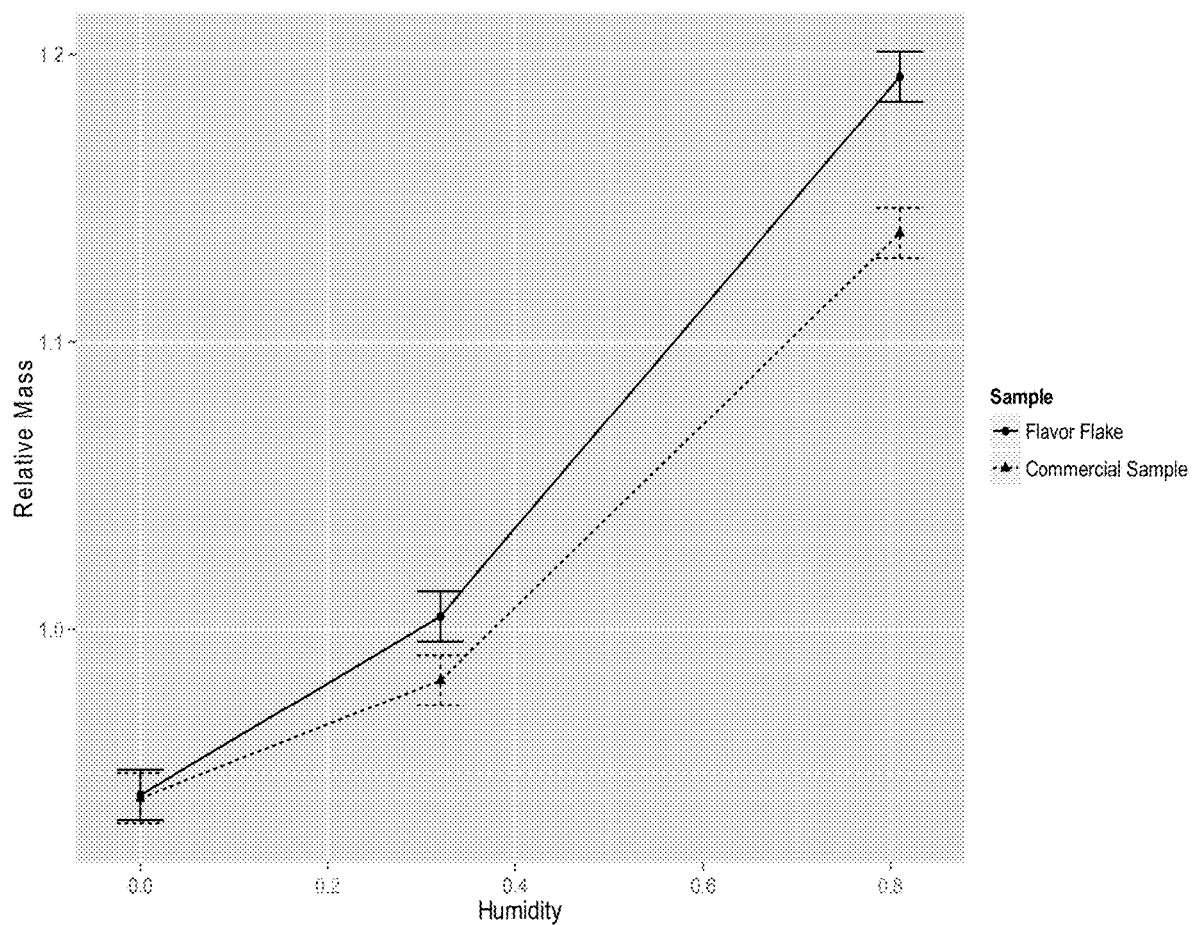
FIG. 4 shows relative mass changes due to absorption of water at two relative humidities: saturated magnesium chloride solution (32% relative humidity), and saturated sodium sulfate solution (81% relative humidity)

Results are summarized in table 1 and FIG. 4. Average relative mass after equilibration is contained in Table 4; these data are plotted in FIG. 4 along with 95% confidence error bars. Both products had a similar mass after equilibration at 0% humidity inferring that they had similar moisture content prior to equilibration. At the other two equilibrium conditions the flavor flake absorbed more water than the commercial sample. Although the beta carotene flake absorbed more water, it was not significantly different from the pre-equilibration mass at 32% humidity. In both cases at 81% humidity both samples were ruined and unusable as an encapsulated active. The similarity of hydration properties of the spray dried and CWD flake at various relative humidities did not explain the observed surprising stability of the CWD flake observed in the shelf-life study of Example 8, below.

TABLE 4

Relative Mass After Equilibration

| Matrix: | Silica Gel (0%) | Magnesium Chloride (32%) | Sodium Sulfate (81%) |
|---|---|---|---|
| Flavor Flake | 94.2% | 100.4% | 119.2% |
| Commercial Spray dried Sample | 94.1% | 98.2% | 113.8% |

Example 12: Controlled Release of Active (beta carotene) from Gum Arabic Matrix

Figure 5:
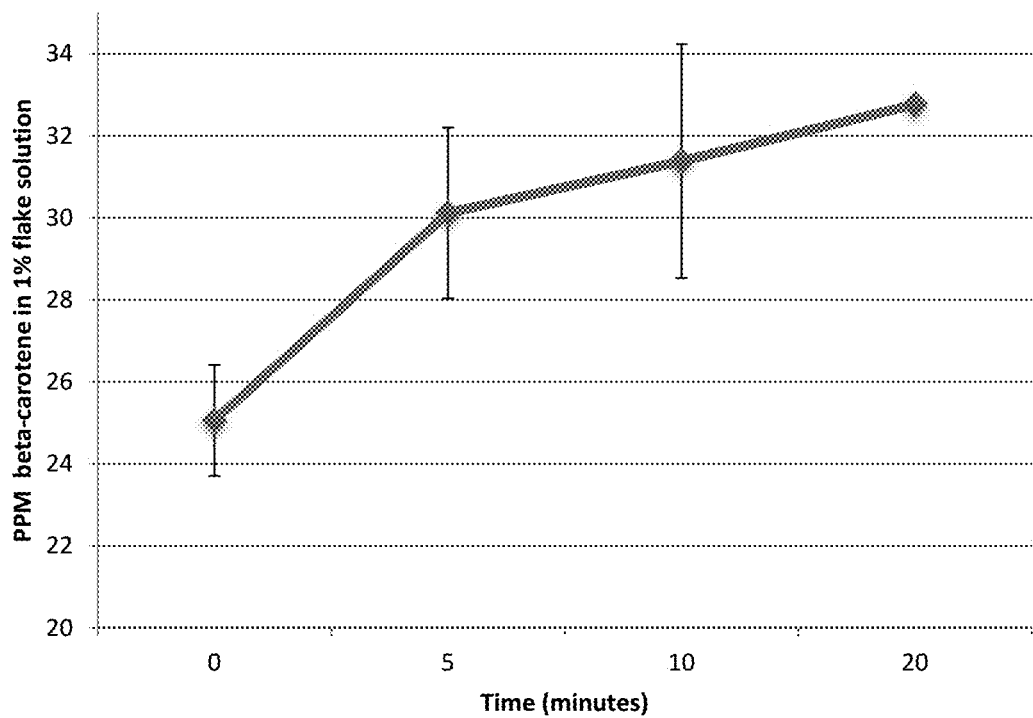
FIG. 5 shows kinetics of beta carotene controlled release.

It is well documented that for spray dried actives (including but not limited to flavors, colors, chemicals that interact in the body), the release rates are dependent on the relative humidity and the composition of the wall materials. The effect of relative humidity on the release of flavor indicates that high retention of flavor is maintained as long as the individual structure of the spray dried sphere remains intact. For active (flavor) flakes produced by the process of FIG. 1, we measured the rate of dissolution of the flakes in water at two temperatures and oil to spectrophotometrically determine when the flake solubilized. The rate of solubilization is a measure of the flake technology's ability to deliver an active under controlled conditions. The solubilization is a function of the carrier, the size and thickness of the flake, the flake porosity and bulk density An active flake was made as in Example 6, above. A 1% (w/w) solution of beta-carotene in water was made. Samples were taken at 0, 5, 10, 20, and 40 minutes on the first trial and 0, 5, and 10 minutes on the replicate. To take a sample the mixture was stirred for ten seconds and a 600 uL aliquot was taken. To this aliquot a known amount of dichloromethane (between 3.00 and 4.50 grams) was added and vigorously shaken for 20 seconds. The dichloromethane layer was pipetted into a cuvette and its absorbance was measured at 461 nm. Results are shown in FIG. 5. This experiment demonstrated the release of beta carotene from the flake over time.

Controlled release is a sought after property for the food and nutraceutical industries. The value is lies in delivering actives (flavor, color, bioactive compounds) in a heated food application, extending the flavor of chewing gum, hot filled sauces, etc.). In addition, directly consumed flake (delivered by pouch, tablet, solubilized in water) provides for a delivery mechanism of micronutrients in the human body. Typically oil soluble ingredients are not as bioavailable as expected (Vitamin E example). Since the flake provides an emulsified version of the active oil, we believe it is more similar to the form found in the original plant and therefore is more recognizable and absorbable in the body. Our release of beta carotene suggests that we can deliver an emulsified form of an active to deliver nutrients to the body and fresh flavor to processed foods.

Example 13: Controlled Release of the Volatile Active Blue Chamomile Oil from Multiple Matrices Volatile components of plants are important sources of actives. The high temperatures associated with spray drying can cause such actives to volatilize and/or degrade, yielding a lower percentage encapsulation than initially added. In addition, the rate of active release can be important for delivery of the active in use. Blue chamomile oil is the volatile essential oil distilled from German Chamomile (*Matricaria chamomilla*) containing a volatile bright blue pigment, the hydrocarbon sesquiterpene chamazulene. Blue chamomile oil was encapsulated using a standard CWD protocol with three different matric compositions, summarized in the table below; in all cases the remaining percentage in each matrix was water:

|  | Matrix | | |
| --- | --- | --- | --- |
| Ingredient | G | M | W |
| Gum Arabic | 73% | 20% | 32% |
| Maltodextrin | 7.6% | 60% | 0% |
| Sunflower Lecithin | 0% | 1.4% | 0% |
| Whey Protein | 0% | 0% | 48% |
| Blue Chamomile Oil | 15% | 15% | 15% |

All flake compositions were analyzed using UV-Vis spectroscopy with absorbance vs. concentration validated using a standard curve. Briefly, 2.5 grams of flake was added to 47.5 grams of deionized water and stirred at 150 RPM using a stirring plate. 200 µL aliquots were taken from the flake-water mixture at 0.5, 2.5, 7.5, and 15 minutes. This aliquot was added to 800 µL of methanol and vortexed for 10 seconds to break the emulsion than spun at 16.1 krcf for 10 miuntes in a centrifuge. The methanol layer was pipetted off and analyzed using a UV-Vis spectrometer and analyzed at 603 nm. Measurements were taken for each flake matrix in duplicate. All data were analyzed using analysis of variance with Tukey's honest significant difference. All statistical significance indicates $p<0.05$. See FIG. 10.

Surprisingly, within the margin of error in the experiment 100% of blue chamomile oil was encapsulated in all matrices; despite blue chamomile oil consisting primarily of volatile monoterpenes and sesquiterpenes. In addition, there were significant differences for the release of the blue chamomile between the flake matrices. The matrix consisting primarily of gum had the fastest release, while the protein heavy and starch heavy matrices had a slower release (although not significantly different from one another). This indicates that a CWD flake can efficiently encapsulate essential oils, and the release from the flake can be tuned for a desired application. Furthermore, as different compositional matricies can have the same release pattern this allows a variety of applications the CWD flake can be used in.

Example 14: Stability of Actives Encapsulated in the Flake via a Shelf Life Test The typical industrial method for determining stability of volatile actives is to conduct and accelerated shelf life test. Encapsulated botanical oil containing monoterpenes, monoterpene alcohols, and sesquiterpenes were prepared in two matrices, one gum arabic and one gum arabic+vegetable derived starch according to the following process:

Step 1: the active is dissolved in a stabilizer, in this case vegetable oil. Therefore the essential oil is mixed in vegetable oil to form an oil mixture Step 2: the gum is dissolved in water Step 3: the oil mixture is slowly added to the gum arabic/water mixture using shear mixing Step 4: the resulting shear mixed mixture is applied to the dryer belt as a thin film and drie More specifically, gum arabic was dissolved in water at a ratio of 20:75 w/w respectively to form a matrix mixture. The essential oil containing monoterpenes and sesquiterpenes, both hydrocarbon and oxygenated, was dissolved in vegetable oil, 10:90 w/w to form an active/oil mixture. 5% of the active oil mixture was added to the 20:75 w/w to equal 100% w/w. This mixture was then applied to the dryer and dried at 180-185F with a 28 belt speed (about 3.8 meters/min). The finished dried flake contained 76.9% gum arabic, 3.6% water and 19.23% active with stabilizer.

A cycling heat/cold study in the absence of light was performed.

TABLE 5

| Essential Oil (EO) diluted with stabilizer | | |
| --- | --- | --- |
| Ingredients | % | Trial: % |
| Essential oil (EO) | 10 | 0.63 |
| Vegetable oil | 90 | 5.67 |
| Total | 100 | 6.3 |
| Liquid Formula for creating a flake | | |
| Ingredient | wet weight % | dry weight | dry weight % |
| gum arabic | 20 | 20 | 78.13 |
| water | 75 | 0.6 | 2.34 |
| EO with stabilizer | 5 | 5 | 19.53 |
|  | 100 | 25.6 | 100.00 |

Samples were stored at 10 weeks under the following heat/cold cycle:

Average Daily High: 94.2 F (34.6 C)
Average Daily Low: 55.6 F (13.1 C)
Maximum High: 106 F (41.1 C)
Minimum Low: 48 F (8.9 C)
Average Daily Differential: 38.5 F (21.4 C) Largest Daily Differential: 53 F (29.4 C)

Figure 6:
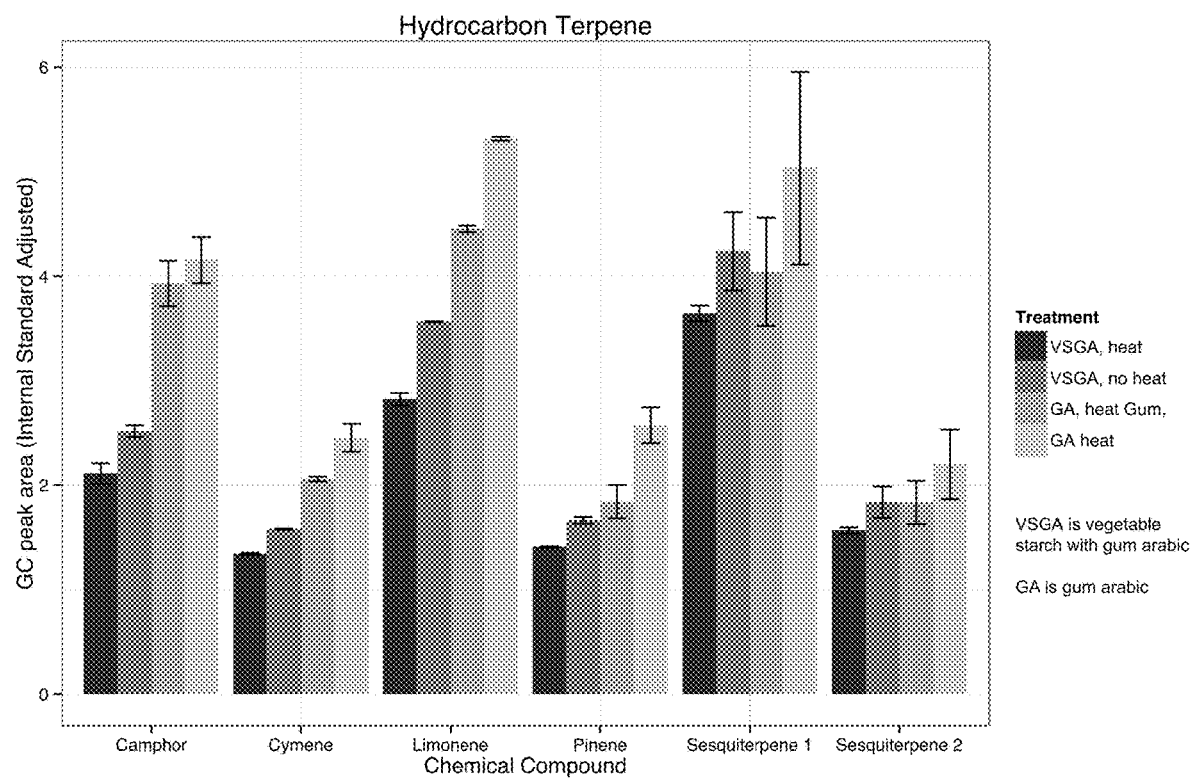
FIG. 6 shows the effect of heated storage on selected hydrocarbon terpenes for two types of flakes demonstrating the effect of the matrix on retention of terpenes during a 70 day shelf-life study.
Figure 7:
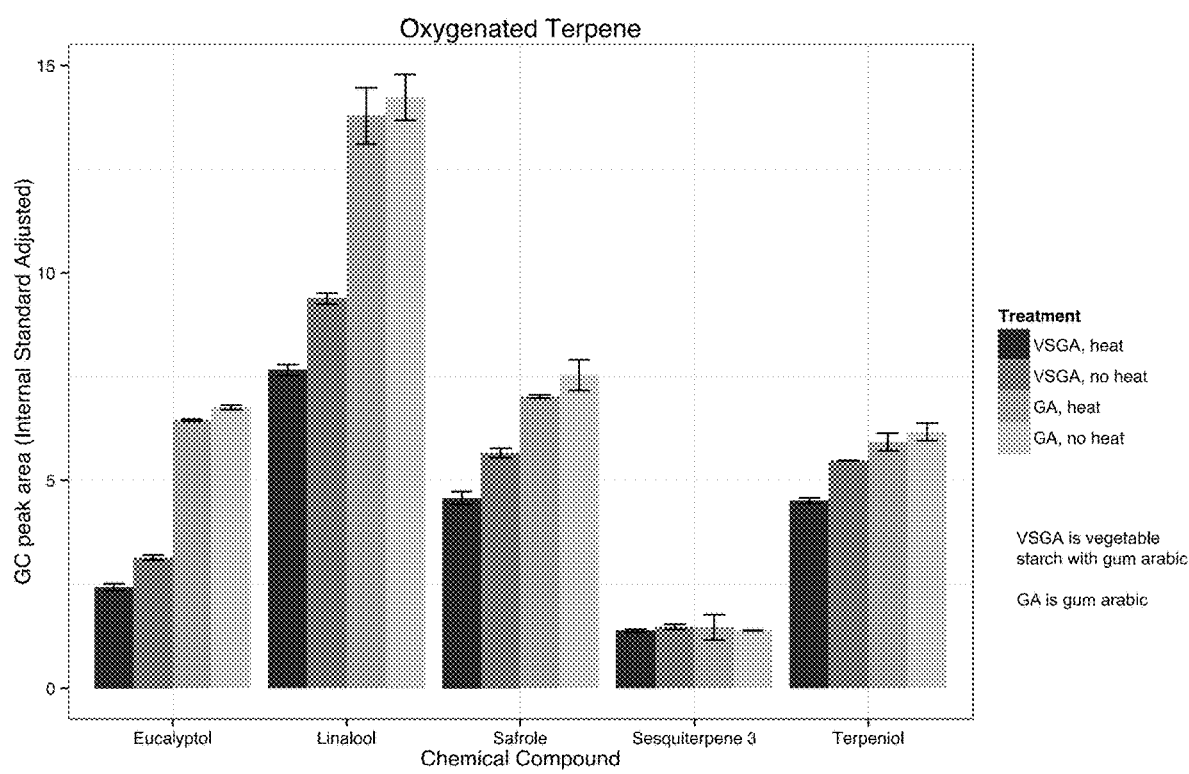
FIG. 7 shows the effect of heated storage on selected oxygenated terpenes for two types of flakes demonstrating the effect of the matrix on retention of oxygenated terpenes during a 70 day shelf-life study.
Figure 8:
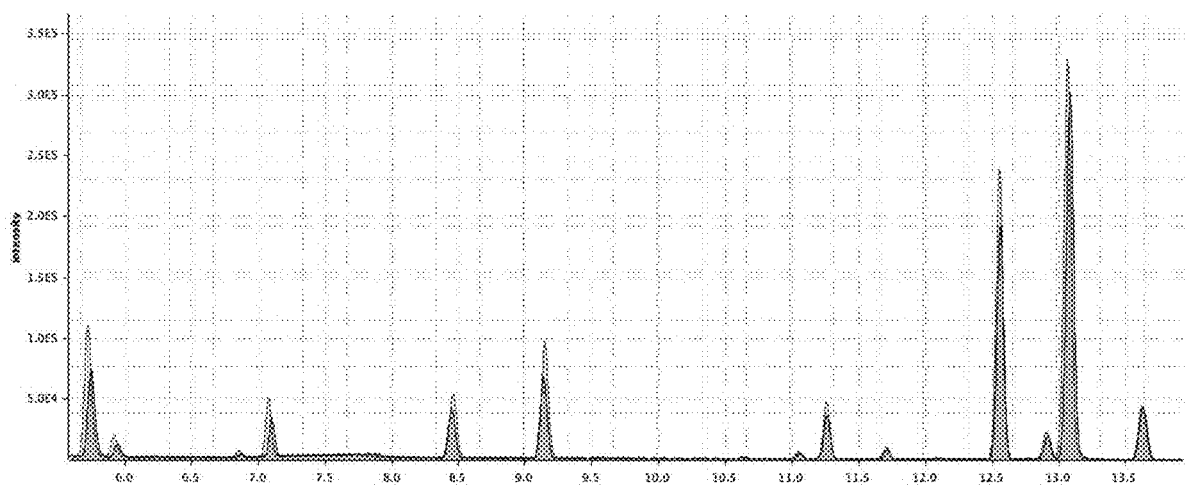
FIG. 8 shows an overlayed chromatogram for the monoterpene fraction of a botanical oil isolated from CWD flakes. The red peaks represent flakes stored at room temperature; black peaks represent flakes stored at accelerated (higher) temperature.
Figure 9:
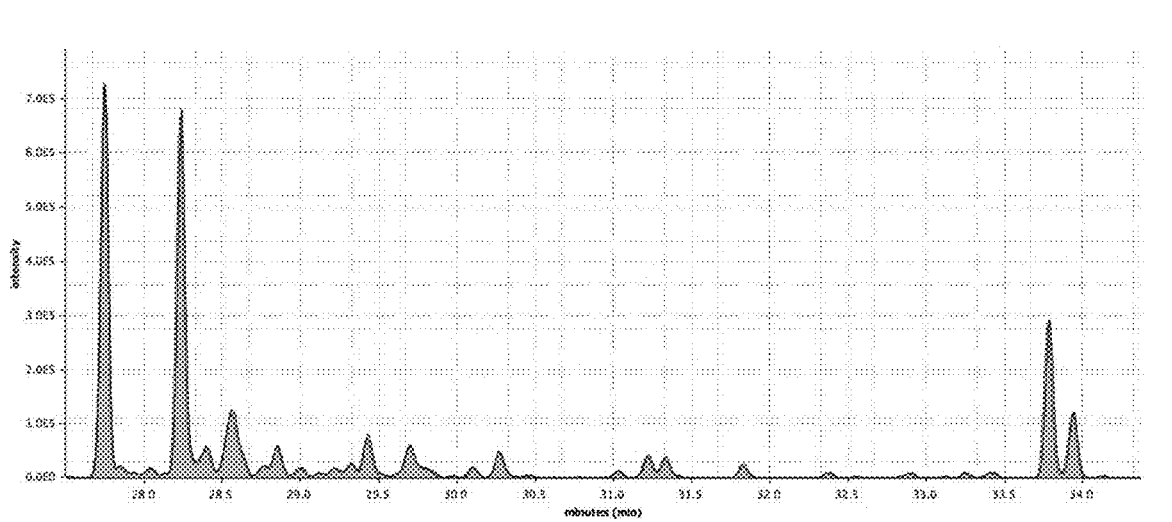
FIG. 9 shows a chromatogram for a oxygenated monoterpene and hydrocarbon sesquiterpene fraction of a botanical oil isolated from CWD flakes in which the red peaks represent the control (room temperature) and the black peaks represent flakes stored at accelerated temperatures.

As in Example 5, we observed that the matrix/carrier impacted the retention of actives; a carrier of gum arabic with vegetable starch retained more actives than the gum arabic alone. During the shelf life study, both matrices (gum arabic or gum arabic with vegetable starch) functioned well and retained the actives of the essential oil tested in this study (FIGS. 6 and 7). For the vegetable starch and gum arabic matrix, the monitored 7 out of 11 compounds did not statistically decrease in concentration over time. For the gum arabic matrix, 8 out of 11 monitored compounds measured did not statistically decrease in concentration during the 10 week cycling temperature abuse. In addition, for the gum arabic matrix, oxygenated monoterpenes such as terpineol, linalool, and eucalyptol did not significantly decrease during the 10 week cycling temperature abuse. This is unexpected as monoterpene actives such as terpineol, limonene etc. are known to oxidize easily and quickly. We saw no oxidation in the dried product over time as evidenced by the lack of new peaks formed in the gas chromatograms depicted in FIGS. 8, 9. (If oxidation was occurring, we would expect to see oxidized terpenes represented as new peaks.) The stability observed in the thin film dried product was unexpected due to the well documented lack of stability of spray dried terpenes.

Five terpenes (linalool, limonene, β-pinene, cymene, and eucalyptol) were compared to literature values for stored spray dried terpenes. In some cases in the literature heat was applied, in some cases heat was not applied. These data are shown in FIGS. 6-9 and are compiled in the table below.

| Compound | Percent Remaining 10 week (70 days) cycling heat with conductance dried) | Literature Storage Conditions | Literature Percent remaining for spray dried terpenes |
|---|---|---|---|
| Linalool | 90% | Heated: 50 C. for 33 days | 25% |
| Limonene | 82% | Heated: 50 C. for 33 days | 53% |
| β-Pinene | 77% | Heated: 50 C. for 33 days | 85% |
| Cymene | 84% | No heat: 25 C. for 42 days | 86% |
| Eucalyptol | 90% | No heat: 25 C. for 42 days | 89% |

The thin film dried samples (stored in hot temperatures) preformed comparably to spray dried samples for the retention of cymene and eucalyptol, stored at room temperature and β-Pinene, stored at hot temperatures The thin film dried sample had much better retention of linalool and limonene than spray dried samples when both samples were stored under conditions of higher temperatures.

Example 15: Using Alcohol as a Stabilizer in the CDW Drying of Parsley Puree

Two different flake preparations were made in accordance to the process of FIG. 1: One with 60 g of fresh parsley, 12 g of gum Arabic, and 72 g of water; the other made with 60 g of fresh parsley, 12 grams of gum Arabic, and 72 g of ethanol-water (60% w/v). All ingredients were ground in a blender, applied to a CDW belt and dried at 175 F with a belt speed of 25%. The fresh parsley (both adaxial and abaxial sides), the flake dried with water, and the flake dried with ethanol-water were analyzed using a Hunter Lab color analyzer. All data were analyzed using analysis of variance with Tukey's honest significant difference. All statistical significance indicates p<0.05. The results are summarized in FIG. 11.

The resulting dried flakes retained a surprisingly bright green color. The color of the water-based parsley flakes were not significantly different from fresh parsley. The color of the ethanol-based parsley flakes were significantly more green and more yellow than the fresh parsley, indicating an even more vibrant color. The color of an ingredient is indicative of high nutritive, flavor and culinary value. The resulting flakes can be used in a dry seasoning blends as colorant, flavorants, and/or sources of nutrients..

Example 16: Using Fermentation as an Ethanol Based Stabilizer for Stabilizing Kiwifruit Derived Actinidin Kiwifruit was subjected to three different treatments then dried with CWD: (1) using no stabilizers prior to drying (RF), (2) fermenting the fruit to produce an ethanol stabilizer prior to drying (FF), and (3) fermenting the fruit to produce an ethanol stabilizer than adding an ammonium hydroxide stabilizer prior to drying (FFS). The enzyme activity of the protease enzyme Actinidain was quantified in each sample. Bound enzyme was quantified using $N_\alpha$-Z-L-lysine 4-nitrophenyl ester (z-Lys-pNP), unbound enzyme was quantified by activating Actinidain with dithiothreitol then quantifying using z-Lys-pNP. The results are summarized in the table below.

Raw fruit (RF) had very low levels of enzyme activity indicating that the enzyme was not preserved during the drying process. Fermented fruit, both without (FF) and with (FFS) an additional stabilizer, had much higher levels of enzyme activity. Furthermore, thin film dried fermented kiwifruit had much higher levels of bound enzyme than a typical commercial process (e.g., freeze drying). The bound enzyme is less sensitive to gastric degradation and can be activated in-vivo in the presence of low concentrations sulfur compounds. This shows that CWD can produce stable formations of an enzyme that has desirable properties that other preparations do not.

| Method | Enzyme Activity (Unbound) | Enzyme Activity (Bound) |
|---|---|---|
| RF | 300 ± 200 | 0 |
| FF | 12400 ± 1500 | 23500 ± 700 |
| FFS | 4900 ± 1000 | 47900 ± 600 |
| Typical Commercial Product | 50000 | 7500 |

Example 17: Making a CBD Containing Hemp Based Active Flake for Rapid Release and Quick Onset of the Psychophysical Response to Said Active in an Erythritol Based Dry Mix Beverage The following process is used:
Step 1: Cannabis oil (hemp oil) is heated
Step 2: the gum is dissolved in water Step 3: the hot cannabis oil is slowly added to the gum Arabic/water mixture using shear mixing Step 4: The resulting sheared mixture is applied to the CWD belt as a thin film and dried.

Note: Such emulsifiers as sunflower lecithin can be used by mixing w/hydrated gum Arabic or directly with cannabis oil→call sunflower lecithin a stabilizer?

Step 5: The flakes are ground with erythritol and put in a sealed packet.

More specifically, gum Arabic was dissolved in water at 25% (w/w) to form a matrix mixture. The cannabis oil containing (80% CBD) and 0% THC was heated with sunflower lecithin and botanical terpenes and added to the gum mixture at 6.5%, 0.2%, and 0.05% (w/w) respectively to equal 100% w/w This mixture was then applied to the dryer and dried @ 180-185 F with a 28 belt speed (about 3.8 meters/min). The finished dried flake contained 19.7% (w/w) oil and 16.3% (w/w) active. The flake is ground with w/erythtiol at 3% to 6% (w/w) and placed in packets. Packets containing active for of 5 mg to 40 mg active were created for a dose/response thresholding study.

The determination of perception of intensity and time of onset was used as a measurement for bioactive release and absorption using a group of experienced sensory panelists. The flake erythritol mix in a sachet/envelope was given to panelists. Each of the eight panelists received 4 samples w/varying amounts of CBD flakes: 5 mg, 10 mg, 20 mg, and 40 mg. They were asked to put the contents of the pouch into the provided container and add 3 fluid ounces of water and drink w/not having consumed caffeine within 1 hour and having eaten within the previous hour. Each dose was consumed at minimum 8 hours apart.

The panelists completed a ballot indicating their characterization of the intensity and quality of the effect at 15 and 30 minutes after they ingested the flakes/erythritol/water mix. Intensity was measured using a five point scale on effect intensity (None, Low, Moderate, High, Very High) and quality was quantified using a list of descriptors to describe the perception of feeling, these descriptors were: increased relaxation, increased focus, decreased anxiety decreased stress, decreased pain, and centered. Intensity data were analyzed using a three-way (panelist, time, concentration) analysis of variance with Tukey's honest significant difference ($p<0.05$). Quality data were analyzed using a chi-square test at ($p<0.05$). The results of the data are summarized in FIG. 12 and FIG. 13.

Both the time and dosage factors were significant ($p<0.05$) in the analysis of variance, no interaction factors were significant ($p>0.05$). These results indicate that the intensity of the effect is increasing with time and quantity of CBD consumed; within 30 minutes post-consumption the 20 mg and 40 mg doses had a stronger effect than 5 mg and 10 mg doses. The only perceived quality that significantly differed from the others was "Increased Relaxation" ($p<0.05$). These results are surprising because many other studies have indicated that it takes a considerably longer time to feel the effect of oral CBD and higher doses are required. FIG. 14 compares this RWD encapsulated CBD study with published studies that have similar numbers of subjects and monitored subjective effects of CBD over time. The perceived effects of CBD were observed much faster and at lower doses with RWD, furthermore, only the two higher dose studies had a significantly effect on relaxation. Thus, it can be inferred that CWD encapsulated CBD may be bioactive post-consumption 2 to 4 times faster at a 20 to 30 times lower dosage concentration.

Example 18: Making a THC Containing Marijuana Based Active Flake for Release/Onset the Psychophysical Response to Said Active in a Fiber Based Oral Pouch The following procedure is followed:
Step 1: Cannabis oil is heated
Step 2: gum arabic is dissolved in water
Step 3: the hot cannabis oil is slowly added to the gum Arabic/water mixture using shear mixing
Step 4: The resulting sheared mixture is applied to the CWD belt as a thin film and dried.
Note: Such stabilizers as sunflower lecithin can be used by mixing w/hydrated gum Arabic or directly with cannabis oil.
Step 5 The flakes are ground+used in generic oatmeal cookie formula. Flakes are incorporated into dry flour/salt/baking said. Oil is incorporated into the batter used in a control cookie.

More specifically, gum Arabic was dissolved in water at 25% (w/w) to form a matrix mixture. The cannabis oil containing (90% THC) was heated with sunflower lecithin and botanical terpenes and added to the gum mixture at 6.2%, 0.2%, and 0.05% (w/w) respectively to equal 100% w/w This mixture was then applied to the dryer and dried @ 180-185 F with a 28 belt speed (about 3.8 meters/min). The finished dried flake contained 18.9% (w/w) oil and 17.0% (w/w) active. This flake was added to a pouch containing plant fiber, oil, glycerin, and flavoring at a level where each pouch contained 10 mg of THC.

The determination of perceived intensity and time of onset time was used as a measurement for bioactive release and absorption using a group of consumers. A pouch was given to each of 20 consumers of cannabis. Consumers were instructed to not consume alcohol or tobacco products for 8 hours prior to the usage of the pouch. Consumers were asked to put the pouch in their mouth and begin monitoring the subjective feeling of the cannabis product.

The Consumers completed a ballot indicating the subjective characterization of the intensity at 10, 20, and 30 minutes post-oral placement. Intensity was measured using a five-point scale on effect intensity (None, Low, Moderate, High, Very High). This data was analyzed using Bayesian multinomial estimation with Jeffery's prior to determine the proportion of consumers with psychophsycal response greater than a given intensity threshold. All data are reported as 95% credible highest density intervals. This data is summarized in FIG. 15.

The intensity data estimates that over 50% of consumers will feel the effects of the RWD THC flake in pouch at 10 minutes, over 70% at 20 minutes, and over 80% at 30 minutes. In addition over 50% of consumers will have a moderate strength or greater effect at 20 minutes, and over 70% will have a moderate strength effect or at 30 minutes. Much like with CBD, the onset of effect of THC is surprising as it is commonly accepted that the effects of low-dose oral THC do not begin until 30 minutes post consumption.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A process for producing a dried product optionally in the form of a flake, the process comprising:
   (a) combining about 0.01-30 wt. % of a terpene, a carrier comprising about 5-50 wt. % gum arabic, and water, to create a liquid wet mixture in which the terpene is emulsified in the carrier;
   (b) spreading the wet mixture on a belt of a thin film belt dryer with a belt temperature in the range of about 60° C.-92° C.; and
   (c) drying the mixture to produce a dried product with less than about 7% moisture and having a water activity of about 0.15 and about 0.65.

2. The process of claim 1, wherein the carrier is hydrophilic, and the terpene is dispersed and embedded in the hydrophilic carrier in the dried product, and wherein the dried product comprises at least about 0.01 wt. % of the terpene, or at least about 100-times the detection threshold of a flavor compound as determined using ASTM method E-679.

3. The process of claim 1, wherein the carrier is hydrophilic and the terpene is dispersed in globules embedded in the hydrophilic carrier, and the globules are predominantly less than about 10 microns in diameter.

4. The process of claim 1, wherein the dried product absorbs less than about 10% water by mass when exposed to a vapor of excess magnesium chloride solution (32% relative humidity) in an air-tight container for 1 week; and less than about 30% water by mass when exposed to a vapor of saturated sodium sulfate solution (81% relative humidity) in an air-tight container for 1 week.

5. The process of claim 1, wherein the dried product is a flake that is between about 0.07 and 1000 microns thick.

6. The process of claim 1, wherein the carrier further comprises a protein, inulin, a starch, or an oligosaccharide.

7. The process of claim 1, wherein the carrier further comprises maltodextrin, corn starch, potato starch, a sugar, lactose, dextrose, whey protein, microalgal protein, hemp protein, yeast or a combination thereof.

8. The process of claim 1, wherein the wet mixture further comprises steric acid or ethanol.

9. The process of claim 1, wherein the terpene comprises a monoterpene.

10. The process of claim 9, wherein the terpene comprises limonene, citral, menthol, menthone, camphor, citronellol, citronellal, geraniol, gerol, alpha-pinene, beta-pinene, citral, linalool, alpha-terpineol, alpha-phellanderene, sabinene, thymol, cymene, or myrcene.

11. The process of claim 1, wherein the terpene comprises a sesquiterpene.

12. The process of claim 11, wherein the terpene comprises beta-caryophylenne, alpha-humulene, or nootkatone.

13. The process of claim 1, wherein the terpene comprises a diterpene.

14. The process of claim 13, wherein the terpene comprises phytol, steviol glycosides, retinol, or retinal.

15. The process of claim 1, wherein the terpene comprises a tetraterpene.

16. The process of claim 15, wherein the terpene comprises alpha-carotene, beta-carotene, gamma-carotene, lycopene, lutein, zeaxanthin, neoxanthin, violaxanthin, flavoxanthin, alpha-cryptoxanthin, or beta-cryptoxanthin.

17. The process of claim 1, wherein the terpene is a triterpene, diterpene glycoside, or a triterpene glycoside.

18. The process of claim 1, wherein the wet mixture comprises about 10-50 wt. % gum arabic and about 1-30 wt. % of a terpene based on the weight of the wet mixture.

19. The process of claim 1, wherein the wet mixture further comprises lecithin.

20. The process of claim 1, wherein the wet mixture further comprises a cannabinoid.

21. The process of claim 1, wherein the wet mixture further comprises tetrahydrocannabinol (THC), cannabidiol (CBD), cannabinol (CBN), cannabigerol (CBG), tetrahydrocannabivarin (THCV), cannabidivarin (CBDV), or cannabichromene (CBC).

22. The process of claim 1, wherein the wet mixture comprises a *Cannabis* extract.

23. The process of claim 22, wherein the *Cannabis* extract is a supercritical carbon dioxide, butane, ethanol, ethyl acetate, or isopropyl alcohol extract of *Cannabis*.

24. The process of claim 1, wherein the wet mixture comprises:
   about 1% to 30% (w/w) *Cannabis* extract;
   about 10% to 30% (w/w) gum arabic; and
   about 1% to 30% (w/w) added terpene.

25. The process of claim 1, wherein the dried product when rehydrated in a solvent for the carrier forms a stable emulsion of the terpene in the solvent.

* * * * *